US007585950B2

(12) United States Patent
Odell

(10) Patent No.: US 7,585,950 B2
(45) Date of Patent: Sep. 8, 2009

(54) PLANT MYB TRANSCRIPTION FACTOR HOMOLOGS

(75) Inventor: Joan T. Odell, Unionville, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/960,847

(22) Filed: Dec. 20, 2007

(65) Prior Publication Data

US 2008/0102471 A1 May 1, 2008

Related U.S. Application Data

(60) Continuation of application No. 11/687,962, filed on Mar. 19, 2007, now abandoned, which is a division of application No. 10/659,869, filed on Sep. 11, 2003, now Pat. No. 7,193,132, which is a continuation of application No. 10/021,811, filed on Dec. 14, 2001, now abandoned, which is a division of application No. 09/452,244, filed on Dec. 1, 1999, now abandoned.

(60) Provisional application No. 60/110,609, filed on Dec. 2, 1998.

(51) Int. Cl.
*C07K 14/00* (2006.01)

(52) U.S. Cl. .................... 530/370; 530/350; 530/378

(58) Field of Classification Search .................. None
See application file for complete search history.

(56) References Cited

U.S. PATENT DOCUMENTS 5,968,793 A 10/1999 Liu et al.

FOREIGN PATENT DOCUMENTS

| WO | WO 97/00961 A1 | 1/1997 |
| WO | WO 98/13486 A1 | 4/1998 |
| WO | WO 99/16878 A1 | 4/1999 |

OTHER PUBLICATIONS

Feldbrugge et al., Plant J., vol. 11:1079-1093, PCMYB1, A Novel Plant Protein Containing a DNA-Binding Domain with one MYB Repeat, Interacts in Vivo with a Light Regulatory Promoter Unit (1997).
Jackson et al., Plant Cell, vol. 3(2):115-125, Expression Patterns of MYB Genes from Antirrhinum Flowers (1992).
Paz-Ares et al., Embo J. vol. 16:3553-3558, The Regulatory C1 Locus of Zea Mays Encodes a Protein with Homology to MYB Proto-Oncogene Products and with Structural Similarities to Transcriptional Activators (1987).
NCBI General Identifier No. 1002800, May 27, 1997, Iturriaga et al., A Family of Novel MYB-Related Genes from the Resurrection Plant Craterostigma Plantagineum are Specifically Xpressed in Callus and Roots in Response to ABA or Desiccation.
Iturriaga et al., Plant Mol. Biol., vol. 32(4):707-716, A Family of Novel MYB-Related Genes from the Resurrection Plant Craterostigma Plantagineum are Specifically Xpressed in Callus and Roots in Response to ABA or Desiccation (1998).
NCBI General Identifier No. 1732513, Dec. 17, 1998, Xia et al., Identification of Plant Cytoskeletal, Cell Cycle-Related and Polarity-Related Proteins Using Schizosaccharomyces Pombe.
Xia et al., Plant J., vol. 10(4):761-769, Identification of Plant Cytoskeletal Cell Cycle-Related and Polarity-Related Proteins Using Schizosaccharomyces Pombe (1996).
NCBI General Identifier No. 1841475, Feb. 9, 1998, UIMARI et al., MYB-Like Protein of Pea Flowers with Affinity for Promoters of Phenylpropanoid Genes.
Uimari et al., Plant J., vol. 12(6):1273-1284, MYB28: A MYB-Like Protein of Pea Flowers with Affinity for Promoters of Phenylpropanoid Genes (1997).
NCBI General Identifier No. 2832500, Feb. 3, 1998, Romero et al., One Hundred R2R3-MYB Genes in the Genome of *Arabidopsis thaliana*.
NCBI General Identifier No. 82307, Jul. 24, 1997, Jackson et al., Expression Patterns of MYB Genes from Antirrhinum Flowers.
NCBI General Identifier No. 3941480, Dec. 2, 1998, Kranz et al., Towards Functional Characterisation of the Members of the R2R3-MYB Gene Family from *Arabidopsis thaliana*.
NCBI General Identifier No. 3941528, Kranz et al., Towards Functional Characterisation of the Members of the R2R3-MYB Gene Family from *Arabidopsis thaliana*.
NCBI General Identifier No. 1002788, May 27, 1997, Iturriaga et al., A Family of Novel MYB-Related Genes from the Ressurection Plant Craterostigma Plantagineum are Specifically Xpressed in Callus and Roots in Response to ABA or Desiccation.
NCBI General Identifier No. 1002798, May 27, 1997, Iturriaga et al., A Family of Novel MYB-Related Genes from the Resurrection Plant Craterostigma Plantagineum are Specifically Xpressed in Callus and Roots in Response to ABA or Desiccation.
Peer Bork, Genome Res., vol. 10:398-400, Powers and Pitfalls in Sequence Analysis: The 70% Hurdle (2000).
Cao et al., Biochemistry (Moscow) 66(6) 623-627 (2001).
Moyano et al., Plant Cell, vol. 8:1519-1532, Apparent Redundancy in MYB Gene Function Provides Gearing for the Control of Flavonoid Biosynthesis in Antirrhinum Flowers (1996).
Lacombe et al., Science Journal, vol. 292, pp. 1486-1487 (2001).
Lazar et al., Molecular and Cellular Biology, vol. 8(3), pp. 1247-1252 (1988).
Broun et al., Science, vol. 282 (1998).
Bobb et al., PvAlf, An Embryo-Specific Acidic Transcriptional Activator Enhances Gene Expression from Phaseolin and Phytohemagglutin in Promoters, The Plant Journal 8(3):331-343 (1995).
Jin et al., Multifunctionality and Diversity within the Plant MYB-Gene Family, Plant Molecular Biology 41:577-585 (1999).
NCBI General Identifier No. 1046277, Feb. 9, 1996, A. J. Bobb et al., PvAlf, An Embryo-Specific Acidic Transcriptional Activator Enhances Gene Expression from Phaseolin and Phytohemagglutinin Promoters.
NCBI General Identifier No. 1046278, Oct. 31, 1995, A. J. Bobb et al., PvAlf, An Embryo-Specific Acidic Transcriptional Activator Enhances Gene Expression from Phaseolin and Phytohemagglutinin Promoters.
NCBI General Identifier No. 75107026, Mar. 1, 2004, D. Jackson et al., Expression Patterns of MYB Genes from Antirrhinum Flowers.
Kranz et al., Plant J. vol. 16:263-276, Towards Functional Characterisation of the Members of the R2R3-MYB Gene Family from *Arabidopsis thaliana* (1998).

*Primary Examiner*—Medina A Ibrahim

(57) ABSTRACT

This invention relates to an isolated polypeptide having Myb-related transcription factor activity and fusion proteins comprising the polypeptide.

4 Claims, 7 Drawing Sheets

FIG. 1A

```
                  *                      *                            ***
SEQ ID NO:10   MATTQSCQSRSSACSKAAACFPAAVAVDEEHGHHSHQLKGGAQEEAENDNNKPELRRGPW
SEQ ID NO:14   M-----------------------------------------------------RKGPW
SEQ ID NO:26   MGRPPCC-------------------------------------------DKVGVKKGPW
SEQ ID NO:30   MDK-------------------------------------KQLCNTSQD-PEVRKGPW
SEQ ID NO:32   MDK--------------------------------------K-LGNTSHD-PEVRKGPW
SEQ ID NO:34   MDK-------------------------------------KPCDSS-HD-PEVRKGPW
SEQ ID NO:36   MDK-------------------------------------KQQCKTSQD-PEVRKGPW
SEQ ID NO:42   MST------------------------------IAKRDLSSNEEESELRRGPW
SEQ ID NO:44   M------------------------DGKGAR---SSNTLLSSEDEM-------DLRRGPW
SEQ ID NO:46   M------------------------DEKGAR---SSNTLLSCEDEM-------DLRRGPW
SEQ ID NO:48   MST----------------------------SKSVSSSSEDDNELRRGPW
SEQ ID NO:50   MST----------------------------SKSVSSSSEDDNELRRGPW
SEQ ID NO:54   MGRPPCC-------------------------------------------DKEGVKKGPW
SEQ ID NO:63   MDK-------------------------------------KPC-NSSQD-PEVRKGPW
                1                                                            60
```

FIG. 1B

```
                 **   *                  *       *            **  *      **********  ***   *            **
SEQ ID NO:10     TVDEDLTLVNYIADNGEGRWNNLARAAGLK---RTGKSCRLRWLNYLRPDVKRGNFSADE
SEQ ID NO:14     TEQEDVQLVWFVRLLGERRWDFLAKVSG----LQRSGKSCRLRWVNYLHPGLKRGRMSPEE
SEQ ID NO:26     TPEEDLMLVSYIQEHGAGNWRAVPTNTGLM---RCSKSCRLRWTNYLRPGIKRGNFTEQE
SEQ ID NO:30     TMEEDLILINYIANHGEGVWNSLAKAAGLK---RTGKSCRLRWLNYLRPDVRRGNITPEE
SEQ ID NO:32     TMEEDLILITYIANHGEGVWNSLAKAAGLK---RTGKSCRLRWLNYLRPDVRRGNITPEE
SEQ ID NO:34     IMEEDLILINYIANHGEGVWNSLAKASGLK---RTGKSCRLRWLNYLRPDVRRGNITPEE
SEQ ID NO:36     TMEEDLILMNYIANHGEGVWNSLAKAAGLK---RNGKSCRLRWLNYLRPDVRRGNITPEE
SEQ ID NO:42     TLEEDSLLIHYIARHGEGRWNMLAKSAGLK---RTGKSCRLRWLNYLKPDIKRGNLTPQE
SEQ ID NO:44     TVDEDLTLINYVATHGEGRWNTLALSAGLK---RTGKSCRLRWLNYLRPDVRRGNITLEE
SEQ ID NO:46     TVDEDLTLINYIATHGEGRWNTLALSAGLK---RTGKSCRLRWLNYLRPDVRRGNITLEE
SEQ ID NO:48     TLEEDNLLSQYIFNHGEGRWNLLAKRSGLK---RTGKSCRLRWLNYLKPDVKRGNLTPQE
SEQ ID NO:50     TLEEDNLLSQYISSHGEGRWNLLAKRSGLK---RTGKSCRLRWLNYLKPDVKRGNLTPQE
SEQ ID NO:54     TPEEDIILVSYIQEHGPGNWRAVPAKTGLS---RCSKSCRLRWTNYLRPGIKRGNFTEQE
SEQ ID NO:63     TMEEDLILINYIANHGEGVWNSLAKAAGLK---RTGKSCRLRWLNYLRPDVRRGNITPEE
                 61                                                          120
```

FIG. 1C

```
                   *    ****  **    *      *   *  ***  *** **           *
SEQ ID NO:10   QLLILDLHTRWGNRWSKIAQHLPGRTDNEIKNYWRTRVQKHAKQLNCDANSKRFKDA----
SEQ ID NO:14   ERMVVQLHAKLGNRWSRIAKSIPGRTDNEIKNYWRTHLRK----LKLKQQKQQQSDD----
SEQ ID NO:26   EKLIVHLQALLGNRWAAIASYLPERTDNDIKNYWNTHLKKKLKKMQAAGGGEDSGAASEG
SEQ ID NO:30   QLLIMELHAKWGNRWSKIAKHLPGRTDNEIKNYWRTRIQKHIKQAE-N-FQQQISN----
SEQ ID NO:32   QLLIMELHAKWGNRWSKIAKHLPGRTDNEIKNYWRTRIQKHLKQAS-SSFQQQSSN----
SEQ ID NO:34   QLLIIELHAKWGNRWSKIAKHLPGRTDNEIKNFWRTRIQKHIKQAE-TSQQHGNSS----
SEQ ID NO:36   QLLIMELHAKWGNRWSKIAQHLPGRTDNEIKNYWRTRIQKHIKQAE-N-FQQQSSN----
SEQ ID NO:42   QLLILELHSKWGNRWSKIAQHLPGRTDNEIKNYWRTRIQKQARQLNIESGSKRFIDA----
SEQ ID NO:44   QLLILELHSRWGNRWSKIAQYLPGRTDNEIKNYWRTRVQKHAKQLKCDVNSKQFKDT----
SEQ ID NO:46   QLLILELHSRWGNRWSKIAQYLPGRTDNEIKNYWRTRVQKHAKQLKCDVNSKQFKDT----
SEQ ID NO:48   QLIILELHSKWGNRWSKIAQHLPGRTDNEIKNYWRTRIQKQARHLKIYTDSREFQEL----
SEQ ID NO:50   QLIILELHSKWGNRWSKIAQNLPGRTDNEIKNYWRTRIQKQARHLKIDTDTREFQEL----
SEQ ID NO:54   EKMIIHLQDLLGNRWAAIASYLPQRTDNDIKNYWNTHLRKKLKKMQAGGEG---------
SEQ ID NO:63   QLLIMELHSKWGNRWSKIAKHLPGRTDNEIKNFWRTRIQKHIKQVD-NPNQQNFQQK----
               121                                                       180
```

FIG. 1D

```
              *        *  *                                                                                    *
SEQ ID NO:10  ---------------------------------------MRYLWMPHLADDVDTIAAANDDD-EDHHHNLRLLVLHHHQAQ
SEQ ID NO:14  ----------------------------------HH------NDNDDDDDRNSS-SSSSSSNSNLQQQPQ-
SEQ ID NO:26  GGGRGDGDGGGKSVKAAAPKGQWERRLQTDIHTARQALRDALS------LDHPDPSPAT
SEQ ID NO:30  ----------------------------------------------NSEINDHQAS---TSHVSTMAEPMETYSPPF
SEQ ID NO:32  ----------------------------------------------SEIIYHPQAC---TSQVSTMAQPIETYSPPS
SEQ ID NO:34  ----------------------------------------------ENSNNDHQASNS-TSKVSTMAHPNETFSSPS
SEQ ID NO:36  ----------------------------------------------NSEINDHQAS---TSHVSTMAEPMEMYSPPC
SEQ ID NO:42  --------------------------------------XKCFWMPRLLQK--MEQSNSP---SPHHSSM-------TNMM
SEQ ID NO:44  --------------------------------------MRYIWMPRLVE---------RI-QATAAASAPQPVTVPPRP
SEQ ID NO:46  --------------------------------------MXYLXXXKARG-THSSSGDGPRN-HHRNCGRHQQCIHLRXQP
SEQ ID NO:48  --------------------------------------VRRFWMPRLLQK--AKESSSSNM-SIQNQAIPMPFDYVSQHL
SEQ ID NO:50  --------------------------------------VRRFWMPRCFKK--PKNH------LLQPCQFKTRQL
SEQ ID NO:54  -GSFGEGFSASRQI-------------------------PRGQWERRLQTDIQMAKRALSEALSPEKKPSCLSASNSNPSD
SEQ ID NO:63  ----------------------------------MS------LEINDHHHHHPHQPS-SSQVSNLVEPMETYSPTS
              181                                                                                              240
```

FIG. 1E

```
             HLQQAAAAGGAANDLAAGAYDVRQL---HALPSSGMAATSSSDSLASESYDDGGLLFAN
SEQ ID NO:10 -----PEDE-----SSASGSLQAQHHEDQHQLFLH-PLWNDDIIVDVDCWSSSTNVVA
SEQ ID NO:14 AAAAATPAGSSAA----YASSADNIARLLQGWMR--PGGGGGGNGKGPEA----SGSTST
SEQ ID NO:26 YQGML-------------------------------------------------EPFSS------
SEQ ID NO:30 YQGML-------------------------------------------------DPFS-------
SEQ ID NO:32 YQATF-------------------------------------------------EPFQP------
SEQ ID NO:34 YQGML-------------------------------------------------EPFST------
SEQ ID NO:36 NLGNSG---EASMSSMSSSFNINPSMSSSSSPPKGNLLWM--------MP------NHF-
SEQ ID NO:42 --------------------------------------------------TMHTPTEAT
SEQ ID NO:44 YTTKFEVLNHKGRMGLTDPSVANNDFVGSHVTQRYPTPENSSTGASSSDSFGTQVSTISD
SEQ ID NO:46 TVGTIPPWQGPCMNEAGPTYMDQHEQTQTRNTNNGSCISLSESANIPKVP----QHFG
SEQ ID NO:48 L-------CLLMV----FLS-------------------------IQL------
SEQ ID NO:50 SSSSFSSTKPTTTQSVCYASSADNIARMLKGWMKNPPKSSRTNSSMTQNSFNNLAGADTA
SEQ ID NO:54 YQGTL-----------------------------------------EPF-p------
SEQ ID NO:63
             241                                                        300
```

FIG. 1F

```
SEQ ID NO:10   LRAGEMLMDGGDWAAQQEADQGL------WPPPPPPSDLDQSVVQAAGAGAGQFQ----D
SEQ ID NO:14   PP------------------------------PM------------------------PAS---
SEQ ID NO:26   TATTQQQPQCSGEGAASA--------------SASASQSGAAAAATAQT---------PECS
SEQ ID NO:30   ------------------------------------------------------IQFP----T
SEQ ID NO:32   ------------------------------------------------------IQFP----T
SEQ ID NO:34   ---------------------------------------------------------QFL---Q
SEQ ID NO:36   ---------------------------------------------------------QFP----T
SEQ ID NO:42   -----KYYVQ----PHQSIPRF-----------LPIFTAT--------------------
SEQ ID NO:44   L-----------------------------------ITTNSRFTITRA---------------
SEQ ID NO:46   LTENSSVPENTNSADY--YQPSQISNY---SDNCITSPSGFLFPQGLDLQSMD----------
SEQ ID NO:48   HTTITQFHAL----NTNDFGTFTYEGYN--VNNNVYEMDNFKTTTWVAEDAQYPIGDCQ
SEQ ID NO:50   ---LGPYHHI-----HT-------------------------------------PLG------
SEQ ID NO:54   CSSGAKGPLSSAELSENNFESL----FDFDQSLESSNSDQFSQSLS---------PEAT
SEQ ID NO:63   --------------------------------------------------------TQFP----T
               301                                                          360
```

FIG. 1G

```
                         *                                                            *
SEQ ID NO:10    MELSGWV-------QGFSESITDNFWALEEIWKMQ.------------------------
SEQ ID NO:14    ---PLWDID----DAFFCSDYSLPLWG.-------------------------------
SEQ ID NO:26    TETSK---MATGGGAGGPAPAFSMLESWLLDDGGMGLMDVVPLGDPSEFF----------
SEQ ID NO:30    INPDQ------SSCCTNDNNNSINYWSMEDIWSMQLLN---GD.----------------
SEQ ID NO:32    -NPHH------SSCCTNDDDDN-NYWSMEDIWSMQL-A---NY.----------------
SEQ ID NO:34    SMINQ------VVVPATT-----TIGASRISGRLC---NYSMEIN---------------
SEQ ID NO:36    INPDQ------SSCCTNDNNN-INYWSMEDSWSMQLLN---G------D-----------
SEQ ID NO:42    ---KWG------------------------------------------------------
SEQ ID NO:44    -PNTPWNMQSGDSSDN-------FWDVESMLFLEQQL----MNDNM--------------
SEQ ID NO:46    MVGSNWV-----------------NNDFACNMWNMDELWQFSKLQ---------K-----
SEQ ID NO:48    ----------------------------------RDLV.--------------------
SEQ ID NO:50    VLQDE---SKPDINIAAEIMPFSLLEKWLLDEAGCQEKLVGCCGDAK-FF----------
SEQ ID NO:54    INNDH-----HQNSNCCANDNNNN-NYWSMEDIWSMQLLN---G------D---------
SEQ ID NO:63
                361                                                        410
```

PLANT MYB TRANSCRIPTION FACTOR HOMOLOGS

This application is a Continuation of U.S. application Ser. No. 11/687,962, filed Mar. 19, 2007, now abandoned, which is a Divisional of U.S. application Ser. No. 10/659,869, filed Sep. 11, 2003, now U.S. Pat. No. 7,193,132, issued Mar. 20, 2007, the entire contents of which are herein incorporated by reference, which was a Continuation of U.S. application Ser. No. 10/021,811, filed Dec. 14, 2001, now abandoned, which was a Divisional of U.S. application Ser. No. 09/452,244, filed Dec. 1, 1999, now abandoned, which claimed the benefit of U.S. Provisional Application No. 60/110,609, filed Dec. 2, 1998, now expired.

FIELD OF THE INVENTION

This invention is in the field of plant molecular biology. More specifically, this invention pertains to nucleic acid fragments encoding Myb-related transcription factors in plants and seeds.

BACKGROUND OF THE INVENTION

Improvement of crop plants for a variety of traits, including disease and pest resistance, and grain quality improvements such as oil, starch or protein composition, can be achieved by introducing new or modified genes (transgenes) into the plant genome. Transcriptional activation of genes, including transgenes, is in general controlled by the promoter through a complex set of protein/DNA and protein/protein interactions. Promoters can impart patterns of expression that are either constitutive or limited to specific tissues or times during development.

Transcriptional activation is primarily mediated through transcription factors that interact with enhancer and promoter elements. Binding of transcription factors to such DNA elements constitutes a crucial step in transcriptional initiation. Each transcription factor binds to its specific binding sequence in a promoter and activates expression of the linked coding region through interactions with coactivators and/or proteins that are a part of the transcription complex.

Several plant genes have been identified that appear to encode transcription factors structurally related to the cMyb protooncogene family of mammals. Central to the similarities shared by these proteins is the Myb repeat DNA-binding domain containing conserved tryptophan residues at certain positions, and a helix-turn-helix-related domain. Generally, Myb-related proteins from plants contain two of these repeats, R2 and R3 (Kranz et al. (1998) *Plant J* 16:263-276), though proteins having only one repeat have been identified (e.g., Feldbrugge et al. (1997) *Plant J* 11:1079-1093). These Myb-related genes appear to encode a large family of plant transcription factors that are involved in a diversity of gene regulation. For example, plant Myb-related genes have been shown to regulate anthrocyanin biosynthesis in maize and phenylpropanoid metabolism, disease resistance (WO9813486-A1), expression of gibberellin-regulated genes (WO9700961-A1), expression of stress-related genes (WO9916878-A1), active carbohydrate secretion and flavonol metabolism in antirrhinum flowers (Jackson et al. (1992) *Plant Cell* 3(2):115-125). The first plant transcription activator gene described at the molecular level was the maize c1 gene which encodes a Myb protein (Paz-Ares et al. (1987) *EMBO J.* 16:3553-3558) involved in regulating anthocyanin biosynthesis by trans-activating genes such as c2, A1 and Bz1 which encode enzymes involved in the pathway.

There is a great deal of interest in identifying the genes that encode proteins involved in transcriptional regulation in plants. These genes may be used in plant cells to control gene expression constitutively, in specific tissues or at various times during development. Accordingly, the availability of nucleic acid sequences encoding all or a portion of a Myb-related transcription factor would facilitate studies to better understand gene regulation in plants and provide genetic tools to enhance or otherwise alter the expression of genes controlled by Myb-related transcription factors.

SUMMARY OF THE INVENTION

The present invention relates to isolated polynucleotides comprising a nucleotide sequence encoding a first polypeptide of at least 50 amino acids that has at least 80% identity based on the Clustal method of alignment when compared to a polypeptide selected from the group consisting of a corn Myb-related transcription factor polypeptide of SEQ ID NO: 2, a rice Myb-related transcription factor polypeptide of SEQ ID NO: 12, and a wheat Myb-related transcription factor polypeptide of SEQ ID NO: 56. The present invention also relates to isolated polynucleotides comprising a nucleotide sequence encoding a first polypeptide of at least 50 amino acids that has at least 85% identity based on the Clustal method of alignment when compared to a polypeptide selected from the group consisting of a corn Myb-related transcription factor polypeptide of SEQ ID NO: 8, and a soybean Myb-related transcription factor polypeptide of SEQ ID NO: 28. The present invention also relates to isolated polynucleotides comprising a nucleotide sequence encoding a first polypeptide of at least 50 amino acids that has at least 90% identity based on the Clustal method of alignment when compared to a rice Myb-related transcription factor polypeptide of SEQ ID NO: 16. The present invention also relates to isolated polynucleotides comprising a nucleotide sequence encoding a first polypeptide of at least 50 amino acids that has at least 95% identity based on the Clustal method of alignment when compared to a soybean Myb-related transcription factor polypeptide of SEQ ID NO: 52. The present invention also relates to isolated polynucleotides comprising a nucleotide sequence encoding a first polypeptide of at least 100 amino acids that has at least 80% identity based on the Clustal method of alignment when compared to a polypeptide selected from the group consisting of a corn Myb-related transcription factor polypeptide of SEQ ID NO: 6, a rice Myb-related transcription factor polypeptide of SEQ ID NO: 14, a soybean Myb-related transcription factor polypeptide of SEQ ID NO: 50, and a wheat Myb-related transcription factor polypeptide of SEQ ID NO: 58. The present invention also relates to isolated polynucleotides comprising a nucleotide sequence encoding a first polypeptide of at least 100 amino acids that has at least 85% identity based on the Clustal method of alignment when compared to a wheat Myb-related transcription factor polypeptide of SEQ ID NO: 60. The present invention also relates to isolated polynucleotides comprising a nucleotide sequence encoding a first polypeptide of at least 100 amino acids that has at least 90% identity based on the Clustal method of alignment when compared to a polypeptide selected from the group consisting of a corn Myb-related transcription factor polypeptide of SEQ ID NO: 4, a corn Myb-related transcription factor polypeptide of SEQ ID NO: 10, a rice Myb-related transcription factor polypeptide of SEQ ID NO: 22, a rice Myb-related transcription factor polypeptide of SEQ ID NO: 24, and a wheat Myb-related transcription factor polypeptide of SEQ ID NO: 62. The present invention also relates to isolated polynucleotides comprising a nucleotide sequence encoding a first polypeptide of at least 100 amino acids that has at least 95% identity based on the Clustal method of alignment when compared to a polypeptide selected from the group consisting of a rice Myb-related transcription factor polypeptide of SEQ ID NO: 18 and a rice Myb-related transcription factor polypeptide of SEQ ID NO: 20. The present invention also relates to isolated polynucleotides comprising a nucleotide sequence encoding a first polypeptide of at least 150 amino acids that has at least 80% identity based on the Clustal method of alignment when compared to a polypeptide selected from the group consisting of a rice Myb-related transcription factor polypeptide of SEQ ID NO: 26, a soybean Myb-related transcription factor polypeptide of SEQ ID NO: 34, a soybean Myb-related transcription factor polypeptide of SEQ ID NO: 38, a soybean Myb-related transcription factor polypeptide of SEQ ID NO: 40, a soybean Myb-related transcription factor polypeptide of SEQ ID NO: 42, a soybean Myb-related transcription factor polypeptide of SEQ ID NO: 48, and a soybean Myb-related transcription factor polypeptide of SEQ ID NO: 54. The present invention also relates to isolated polynucleotides comprising a nucleotide sequence encoding a first polypeptide of at least 150 amino acids that has at least 85% identity based on the Clustal method of alignment when compared to a polypeptide selected from the group consisting of a soybean Myb-related transcription factor polypeptide of SEQ ID NO: 32, a soybean Myb-related transcription factor polypeptide of SEQ ID NO: 44, and a soybean Myb-related transcription factor polypeptide of SEQ ID NO: 46. The present invention also relates to isolated polynucleotides comprising a nucleotide sequence encoding a first polypeptide of at least 200 amino acids that has at least 80% identity based on the Clustal method of alignment when compared to a soybean Myb-related transcription factor polypeptide of SEQ ID NO: 36. The present invention also relates to isolated polynucleotides comprising a nucleotide sequence encoding a first polypeptide of at least 200 amino acids that has at least 85% identity based on the Clustal method of alignment when compared to a soybean Myb-related transcription factor polypeptide of SEQ ID NO: 30. The present invention also relates to an isolated polynucleotide comprising the complement of the nucleotide sequences described above.

It is preferred that the isolated polynucleotides of the claimed invention consist of a nucleic acid sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, and 61 that codes for the polypeptide selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, and 62. The present invention also relates to an isolated polynucleotide comprising a nucleotide sequences of at least one of 60 (preferably at least one of 40, most preferably at one least of 30) contiguous nucleotides derived from a nucleotide sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, and 61 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a Myb-related transcription factor polypeptide of at least 50 amino acids that has at least 80% identity based on the Clustal method of alignment when compared to a polypeptide selected from the group consisting of SEQ ID NOs: 2, 12, and 56. The present invention also relates to a Myb-related transcription factor polypeptide of at least 50 amino acids that has at least 85% identity based on the Clustal method of alignment when compared to a polypeptide selected from the group consisting of SEQ ID NOs: 8 and 28. The present invention also relates to a Myb-related transcription factor polypeptide of at least 50 amino acids that has at least 90% identity based on the Clustal method of alignment when compared to a rice Myb-related transcription factor polypeptide of SEQ ID NO: 16. The present invention also relates to a Myb-related transcription factor polypeptide of at least 50 amino acids that has at least 95% identity based on the Clustal method of alignment when compared to a soybean Myb-related transcription factor polypeptide of SEQ ID NO: 52. The present invention also relates to a Myb-related transcription factor polypeptide of at least 100 amino acids that has at least 80% identity based on the Clustal method of alignment when compared to a polypeptide selected from the group consisting of SEQ ID NOs: 6, 14, 50, and 58. The present invention also relates to a Myb-related transcription factor polypeptide of at least 100 amino acids that has at least 85% identity based on the Clustal method of alignment when compared to a wheat Myb-related transcription factor polypeptide of SEQ ID NO: 60. The present invention also relates a Myb-related transcription factor polypeptide of at least 100 amino acids that has at least 90% identity based on the Clustal method of alignment when compared to a polypeptide selected from the group consisting of SEQ ID NOs: 4, 10, 22, 24, and 62. The present invention also relates to a Myb-related transcription factor polypeptide of at least 100 amino acids that has at least 95% identity based on the Clustal method of alignment when compared to a polypeptide selected from the group consisting of SEQ ID NOs: 18 and 20. The present invention also relates to a Myb-related transcription factor polypeptide of at least 150 amino acids that has at least 80% identity based on the Clustal method of alignment when compared to a polypeptide selected from the group consisting of SEQ ID NOs: 26, 34, 38, 40, 42, 48, and 54. The present invention also relates to a Myb-related transcription factor polypeptide of at least 150 amino acids that has at least 85% identity based on the Clustal method of alignment when compared to a polypeptide selected from the group consisting of SEQ ID NOs: 32, 44, and 46. The present invention also relates to a Myb-related transcription factor polypeptide of at least 200 amino acids that has at least 80% identity based on the Clustal method of alignment when compared to a soybean Myb-related transcription factor polypeptide of SEQ ID NO: 36. The present invention also relates to a Myb-related transcription factor polypeptide of at least 200 amino acids that has at least 85% identity based on the Clustal method of alignment when compared to a soybean Myb-related transcription factor polypeptide of SEQ ID NO: 30.

The present invention relates to a method of selecting an isolated polynucleotide that affects the level of expression of a Myb-related transcription factor polypeptide in a host cell, preferably a plant cell, the method comprising the steps of:

constructing an isolated polynucleotide of the present invention or an isolated chimeric gene of the present invention;

introducing the isolated polynucleotide or the isolated chimeric gene into a host cell;

measuring the level of a Myb-related transcription factor polypeptide in the host cell containing the isolated polynucleotide; and comparing the level of a Myb-related transcription factor polypeptide in the host cell containing the isolated polynucleotide with the level of a Myb-related transcription factor polypeptide in a host cell that does not contain the isolated polynucleotide.

The present invention relates to a method of obtaining a nucleic acid fragment encoding a substantial portion of a Myb-related transcription factor polypeptide gene, preferably a plant Myb-related transcription factor polypeptide gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, and 61 and the complement of such nucleotide sequences; and amplifying a nucleic acid fragment (preferably a cDNA inserted in a cloning vector) using the oligonucleotide primer. The amplified nucleic acid fragment preferably will encode all or a portion of a Myb-related transcription factor amino acid sequence.

The present invention also relates to a method of obtaining a nucleic acid fragment encoding all or a substantial portion of the amino acid sequence encoding a Myb-related transcription factor polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

BRIEF DESCRIPTION OF THE DRAWING AND SEQUENCE DESCRIPTIONS

The invention can be more fully understood from the following detailed description and the accompanying drawing and Sequence Listing which form a part of this application.

FIGS. 1A-1G depict the amino acid alignment between the Myb-related transcription factor encoded by the nucleotide sequences derived from corn clone cta1n.pk0079.e9 (SEQ ID NO: 10), contig assembled from rice clones rr1.pk0027.g9 and rr1.pk077.n9 (SEQ ID NO: 14), rice clone r10n.pk082.c13 (SEQ ID NO: 26), soybean clone sfl1.pk0032.g4 (SEQ ID NO: 30), soybean clone sfl1.pk0086.a9 (SEQ ID NO: 32), soybean clone sfl1.pk0091.a2 (SEQ ID NO: 34), soybean clone sfl1 .pk0091.a2 (SEQ ID NO: 36), soybean clone sfl1.pk0003.a3 (SEQ ID NO: 42), soybean clone srr3c.pk002.k6 (SEQ ID NO: 44), soybean clone ses9c.pk002.o16 (SEQ ID NO: 46), soybean clone s12.pk127.e14 (SEQ ID NO: 48), soybean clone src3c.pk010.i22 (SEQ ID NO: 50), soybean clone sgs4c.pk004.j24 (SEQ ID NO: 54), and a Myb-related transcription factor-encoding nucleic acid fragment from *Pisum sativum* (NCBI General Identification No. 1841475) (SEQ ID NO: 63). Amino acids which are conserved among all and at least two sequences with an amino acid at that position are indicated with an asterisk (*) above them. Dashes are used by the program to maximize alignment of the sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"). Nucleotide SEQ ID NOs: 7, 11, 23, 27, 51, and 55 correspond to nucleotide SEQ ID NOs: 1, 3, 9, 5, 11, and 7, respectively, presented in U.S. Provisional Application No. 60/110,609, filed Dec. 2, 1998. Amino acid SEQ ID NOs: 8, 12, 24, 28, 52, and 56 correspond to amino acid SEQ ID NOs: 2, 4, 10, 6, 12, and 8, respectively, presented in U.S. Provisional Application No. 60/110,609, filed Dec. 2, 1998. The sequence descriptions and Sequence Listing attached hereto comply with the rules governing nucleotide and/or amino acid sequence disclosures in patent applications as set forth in 37 C.F.R. §1.821-1.825.

TABLE 1

Myb-related Transcription Factors

| | | | SEQ ID NO: | |
|---|---|---|---|---|
| Protein | Clone Designation | Status | (Nucleotide) | (Amino Acid) |
| Myb-related Transcription Factor (Corn) | Contig of: csi1n.pk0008.b5 csi1n.pk0028.h7 | Contig | 1 | 2 |
| Myb-related Transcription Factor (Corn) | Contig of: p0008.cb31d06r p0026.ccrbd36rb | Contig | 3 | 4 |
| Myb-related Transcription Factor (Corn) | chpc8.pk0002.d9 | EST | 5 | 6 |
| Myb-related Transcription Factor (Corn) | cta1n.pk0079.e9 | EST | 7 | 8 |
| Myb-related Transcription Factor (Corn) | cta1n.pk0079.e9 | CGS | 9 | 10 |
| Myb-related Transcription Factor (Rice) | rr1.pk077.n9 | EST | 11 | 12 |

TABLE 1-continued

Myb-related Transcription Factors

| | | | SEQ ID NO: | |
|---|---|---|---|---|
| Protein | Clone Designation | Status | (Nucleotide) | (Amino Acid) |
| Myb-related Transcription Factor (Rice) | Contig of: rr1.pk0027.g9 rr1.pk077.n9 | CGS | 13 | 14 |
| Myb-related Transcription Factor (Rice) | rr1.pk088.p6 | EST | 15 | 16 |
| Myb-related Transcription Factor (Rice) | rr1.pk0037.g7 | EST | 17 | 18 |
| Myb-related Transcription Factor (Rice) | rds3c.pk002.c6 | EST | 19 | 20 |
| Myb-related Transcription Factor (Rice) | Contig of: rlr24.pk0090.f5 rlr48.pk0012.c11 | Contig | 21 | 22 |
| Myb-related Transcription Factor (Rice) | rl0n.pk082.c13 | EST | 23 | 24 |
| Myb-related Transcription Factor (Rice) | rl0n.pk082.c13 | CGS | 25 | 26 |
| Myb-related Transcription Factor (Soybean) | sfl1.pk0032.g4 | EST | 27 | 28 |
| Myb-related Transcription Factor (Soybean) | sfl1.pk0032.g4 | CGS | 29 | 30 |
| Myb-related Transcription Factor (Soybean) | sfl1.pk0086.a9 | CGS | 31 | 32 |
| Myb-related Transcription Factor (Soybean) | sfl1.pk0091.a2 | CGS | 33 | 34 |
| Myb-related Transcription Factor (Soybean) | sfl1.pk0105.e6 | CGS | 35 | 36 |
| Myb-related Transcription Factor (Soybean) | sfl1.pk125.p19 | FIS | 37 | 38 |
| Myb-related Transcription Factor (Soybean) | se6.pk0048.a12 | FIS | 39 | 40 |
| Myb-related Transcription Factor (Soybean) | sfl1.pk0003.a3 | CGS | 41 | 42 |
| Myb-related Transcription Factor (Soybean) | srr3c.pk002.k6 | CGS | 43 | 44 |
| Myb-related Transcription Factor (Soybean) | ses9c.pk002.o16 | CGS | 45 | 46 |
| Myb-related Transcription Factor (Soybean) | sl2.pk127.e14 | CGS | 47 | 48 |
| Myb-related Transcription Factor (Soybean) | src3c.pk010.i22 | CGS | 49 | 50 |
| Myb-related Transcription Factor (Soybean) | sgs4c.pk004.j24 | EST | 51 | 52 |
| Myb-related Transcription Factor (Soybean) | sgs4c.pk004.j24 | CGS | 53 | 54 |
| Myb-related Transcription Factor (Wheat) | wr1.pk0139.g11 | EST | 55 | 56 |
| Myb-related Transcription Factor (Wheat) | wr1.pk0139.g11 | FIS | 57 | 58 |
| Myb-related Transcription Factor (Wheat) | wdk3c.pk006.n12 | EST | 59 | 60 |
| Myb-related Transcription Factor (Wheat) | wlm1.pk0027.a5 | EST | 61 | 62 |

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides, of the nucleic acid sequence of the SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, or the complement of such sequences.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, and 61 and the complement of such nucleotide sequences may be used in methods of selecting an isolated polynucleotide that affects the expression of a polypeptide in a plant cell. A method of selecting an isolated polynucleotide that affects the level of expression of a polypeptide (such as a Myb-related transcription factor) in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6× SSC, 0.5% SDS at room temperature for 15 min, then repeated with 2× SSC, 0.5% SDS at 45° C. for 30 min, and then repeated twice with 0.2× SSC, 0.5% SDS at 50° C. for 30 min. A more preferred set of stringent conditions uses higher temperatures in which the washes are identical to those above except for the temperature of the final two 30 min washes in 0.2× SSC, 0.5% SDS was increased to 60° C. Another preferred set of highly stringent conditions uses two final washes in 0.1× SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, most preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least about 50 amino acids, preferably at least about 100 amino acids, more preferably at least about 150 amino acids, still more preferably at least about 200 amino acids, and most preferably at least about 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403-410. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225-236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Underexpression" refers to the production of a gene product in transgenic organisms at levels below that of levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol* 143:277) and particle-accelerated or "gene gun" transformation technology (Klein et al. (1987) *Nature (London)* 327:70-73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several Myb-related transcription factors have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other Myb-related transcription factors, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, and 61 and the complement of such nucleotide sequences may be used in such methods to obtain a nucleic acid fragment encoding a substantial portion of an amino acid sequence of a polypeptide (such as a Myb-related transcription factor. The present invention relates to a method of obtaining a nucleic acid fragment encoding a substantial portion of a polypeptide of a gene (such as Myb-related transcription factor) preferably a substantial portion of a plant polypeptide of a gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, and 61 and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of expression of Myb-regulated genes in those cells, and consequently the phenotype affected by those Myb-regulated genes.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.* 100:1627-1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded Myb-related transcription factors. An example of a vector for high level expression of the instant polypeptides in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319-346, and references cited therein).

In another embodiment, nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several to several hundred KB; see Laan et al. (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nat. Genet.* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci. USA* 86:9402-9406; Koes et al. (1995) *Proc. Natl. Acad. Sci. USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries;l Isolation and Sequencing of cDNA Clones cDNA libraries representing mRNAs from various corn, rice, soybean and wheat tissues were prepared. The characteristics of the libraries are described below.

according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs";

TABLE 2 cDNA Libraries from Corn, Rice, Soybean and Wheat

| Library | Tissue | Clone |
|---|---|---|
| chpc8 | Corn (*Zea mays* L.) (MBS847) 8 Day Old Shoot Treated 8 Hours With PDO Herbicide MK593* | chpc8.pk0002.d9 |
| csi1n | Corn (*Zea mays* L.) Silk** | csi1n.pk0008.b5 |
|  |  | csi1n.pk0028.h7 |
| cta1n | Corn (*Zea mays* L.) Tassel** | cta1n.pk0079.e9 |
| p0008 | Corn (*Zea mays* L.) 3 Week Old Leaf | p0008.cb31d06r |
| p0026 | Corn (*Zea mays* L.) Regenerating Callus (Hi-II 223a and 1129e), 5 Days After Auxin Removal | p0026.ccrbd36rb |
| rds3c | Rice (*Oryza sativa*) Developing Seed From Top of the Plant | rds3c.pk002.c6 |
| rl0n | Rice (*Oryza sativa*) 15 Day Old Leaf** | rl0n.pk082.c13 |
| rlr24 | Resistant Rice (*Oryza sativa*) Leaf 15 Days After Germination, 24 Hours After Infection of Strain *Magnaporthe grisea* 4360-R-62 (AVR2-YAMO) | rlr24.pk0090.f5 |
| rlr48 | Resistant Rice (*Oryza sativa*) Leaf 15 Days After Germination, 48 Hours After Infection of Strain *Magnaporthe grisea* 4360-R-62 (AVR2-YAMO) | rlr48.pk0012.c11 |
| rr1 | Rice (*Oryza sativa*) Root of Two Week Old Developing Seedling | rr1.pk0027.g9 |
|  |  | rr1.pk0037.g7 |
|  |  | rr1.pk077.n9 |
|  |  | rr1.pk088.p6 |
| se6 | Soybean (*Glycine max* L) Embryo, 26 Days After Flowering | se6.pk0048.a12 |
| ses9c | Soybean (*Glycine max* L) Embryogenic Suspension | ses9c.pk002.o16 |
| sfl1 | Soybean (*Glycine max* L) Immature Flower | sfl1.pk0003.a3 |
|  |  | sfl1.pk0032.g4 |
|  |  | sfl1.pk0086.a9 |
|  |  | sfl1.pk0091.a2 |
|  |  | sfl1.pk0105.e6 |
|  |  | sfl1.pk125.p19 |
| sgs4c | Soybean (*Glycine max* L) Seed 2 Days After Germination | sgs4c.pk004.j24 |
| sl2 | Soybean (*Glycine max* L) Two-Week-Old Developing Seedling Treated With 2.5 ppm chlorimuron | sl2.pk127.e14 |
| src3c | Soybean (*Glycine max* L) 8 Day Old Root Infected With Cyst Nematode | src3c.pk010.i22 |
| srr3c | Soybean (*Glycine max* L) 8 Day Old Root | srr3c.pk002.k6 |
| wdk3c | Wheat (*Triticum aestivum* L) Developing Kernel, 14 Days After Anthesis | wdk3c.pk006.n12 |
| wlm1 | Wheat (*Triticum aestivum* L) Seedling 1 Hour After Inoculation With *Erysiphe graminis* f. sp *tritici* | wlm1.pk0027.a5 |
| wr1 | Wheat (*Triticum aestivum* L) Root From 7 Day Old Seedling Light Grown | wr1.pk0139.g11 |

*Application of 2-[(2,4-dihydro-2,6,9-trimethyl[1]benzothiopyrano[4,3-c]pyrazol-8-yl)carbonyl]-1,3-cyclohexanedione S,S-dioxide; synthesis and methods of using this compound are described in WO 97/19087, incorporated herein by reference.
**These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries see Adams et al., (1991) *Science* 252:1651-1656). The resulting ESTs are analyzed using a Perkin Elmer Model 377 fluorescent sequencer.

Determination of complete nucleotide sequence of cDNA inserts may be accomplished by a number of methods well-known to those skilled in the art (Maniatis). For example, this may be accomplished stepwise, wherein oligonucleotides near the 5' or 3' end of the sequence may be synthesized which can then serve as primers for sequencing reactions that will extend the known sequence. Another set of oligonucleotides near the 5' or 3' end of the new sequence in the next round prime another set of sequencing reactions to obtain more sequence information. These steps are repeated until the complete nucleotide sequence is determined.

Example 2

Identification of cDNA Clones cDNA clones encoding Myb-related transcription factors were identified by conducting BLAST (Basic Local Alignment Search Tool; Altschul et al. (1993) *J. Mol. Biol.* 215: 403-410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Myb-Related Transcription Factors

The BLASTX search using the EST sequence from clone cta 1 n.pk0079.e9 revealed similarity of the protein encoded by the cDNA to a Myb-related transcription factor from *Craterostigma plantagineum* (NCBI Identifier No. gi 1002800). The BLASTX search using the EST sequence from clone rr1.pk077.n9 revealed similarity of the protein encoded by the cDNA to a Myb-related transcription factor from *Arabidopsis thaliana* (NCBI Identifier No. gi 1732513). The BLASTX search using the EST sequence from clone sfl1.pk0032.g4 revealed similarity of the protein encoded by the cDNA to a Myb-related transcription factor from *Pisum sativum* (NCBI Identifier No. gi 1841475). The BLASTX search using the EST sequence from clone wr1.pk0139.g11 revealed similarity of the protein encoded by the cDNA to a Myb-related transcription factor from *Arabidopsis thaliana* (NCBI Identifier No. gi 2832500). The BLAST results for each of these ESTs are shown in Table 3:

TABLE 3

BLAST Results for Clones Encoding Polypeptides Homologous to Plant Myb-related Transcription Factors

| Clone | BLAST pLog Score |
|---|---|
| cta1n.pk0079.e9 | 39.00 |
| rr1.pk077.n9 | 27.70 |
| sfl1.pk0032.g4 | 38.50 |
| wr1.pk0139.g11 | 16.00 |

The sequence of a portion of the cDNA insert from clone cta 1 n.pk0079.e9 is shown in SEQ ID NO: 7; the deduced amino acid sequence of this cDNA is shown in SEQ ID NO: 8. The sequence of a portion of the cDNA insert from clone rr1.pk077.n9 is shown in SEQ ID NO: 11; the deduced amino acid sequence of this cDNA is shown in SEQ ID NO: 12. The sequence of a portion of the cDNA insert from clone sfl1.pk0032.g4 is shown in SEQ ID NO: 27; the deduced amino acid sequence of this cDNA is shown in SEQ ID NO: 28. The sequence of a portion of the cDNA insert from clone wr1.pk0139.g11 is shown in SEQ ID NO: 55; the deduced amino acid sequence of this cDNA is shown in SEQ ID NO: 56. BLAST scores and probabilities indicate that the instant nucleic acid fragments encode portions of a Myb-related transcription factor protein.

The BLASTX search using the EST sequences from clones r10n.pk082.c13 and sgs4c.pk004.j24 revealed similarity of the proteins encoded by the cDNAs to a Myb-related transcription factor protein from *Pisum sativum* (NCBI Identifier No. gi 82307). The BLAST results for each of these ESTs are shown in Table 4:

TABLE 4

BLAST Results for Clones Encoding Polypeptides Homologous to Plant Myb-related Transcription Factors

| Clone | BLAST pLog Score |
|---|---|
| r10n.pk082.c13 | 62.50 |
| sgs4c.pk004.j24 | 47.50 |

The sequence of a portion of the cDNA insert from clone r10n.pk082.c13 is shown in SEQ ID NO: 23; the deduced amino acid sequence of this cDNA is shown in SEQ ID NO: 24. The sequence of a portion of the cDNA insert from clone sgs4c.pk004.j24 is shown in SEQ ID NO: 51; the deduced amino acid sequence of this cDNA is shown in SEQ ID NO: 52. BLAST scores and probabilities indicate that the instant nucleic acid fragments encode portions of a Myb-related transcription factor protein.

The BLASTX search using the sequences from clones listed in Table 5 revealed similarity of the polypeptides encoded by the cDNAs to Myb-related transcription factors from different plant species including *Pisum sativum* (NCBI General Identification No. 1841475), *Arabidopsis thaliana* (NCBI General Identification Nos. 3941480 and 3941528), *Craterostigma plantagineum* (NCBI General Identification Nos. 1002796, 1002798, and 1002800), and *Antirrhinum majus* (NCBI General Identification No. 82307). Shown in Table 5 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 5

BLAST Results for Sequences Encoding Polypeptides Homologous to Myb-related Transcription Factors

| Clone | Status | NCBI General Identification No. | pLog Score |
|---|---|---|---|
| Contig of: csi1n.pk0008.b5 csi1n.pk0028.h7 | Contig | 1841475 | 54.40 |
| Contig of: p0008.cb31d06r p0026.ccrbd36rb | Contig | 3941480 | 70.10 |
| chpc8.pk0002.d9 | EST | 1002800 | 44.70 |
| cta1n.pk0079.e9 | CGS | 1002800 | 68.52 |
| Contig of: rrl.pk0027.g9 rrl.pk077.n9 | CGS | 3941480 | 50.00 |
| rrl.pk088.p6 | EST | 3941480 | 22.52 |
| rrl.pk0037.g7 | EST | 1002798 | 79.70 |
| rds3c.pk002.c6 | EST | 1002798 | 62.00 |
| Contig of: rlr24.pk0090.f5 rlr48.pk0012.c11 | Contig | 1002800 | 55.04 |
| rl0n.pk082.c13 | CGS | 82307 | 84.22 |
| sfl1.pk0032.g4 | CGS | 1841475 | 96.52 |
| sfl1.pk0086.a9 | CGS | 1841475 | 92.22 |
| sfl1.pk0091.a2 | CGS | 1841475 | 75.10 |
| sfl1.pk0105.e6 | CGS | 1841475 | 96.40 |
| sfl1.pk125.p19 | FIS | 1841475 | 90.52 |
| se6.pk0048.a12 | FIS | 1002798 | 66.70 |
| sfl1.pk0003.a3 | CGS | 1002796 | 59.70 |
| srr3c.pk002.k6 | CGS | 1002798 | 77.40 |
| ses9c.pk002.o16 | CGS | 1002798 | 73.70 |
| sl2.pk127.e14 | CGS | 1002800 | 60.70 |
| src3c.pk010.i22 | CGS | 1002800 | 57.05 |
| sgs4c.pk004.j24 | CGS | 82307 | 90.52 |
| wrl.pk0139.g11 | FIS | 3941480 | 48.52 |
| wdk3c.pk006.n12 | EST | 1002796 | 43.70 |
| wlm1.pk0027.a5 | EST | 3941528 | 73.70 |

FIGS. 1A-1G present an alignment of the amino acid sequences set forth in SEQ ID NOs: 10, 14, 26, 30, 32, 34, 36, 42, 44, 46, 48, 50, and 54 and the *Pisum sativum* sequence (NCBI General Identification No. 1841475; SEQ ID NO: 63). The data in Table 6 represents a calculation of the percent identity of the amino acid sequences set forth in SEQ ID NOs: 10, 14, 26, 30, 32, 34, 36, 42, 44, 46, 48, 50, and 54 and the *Pisum sativum* sequence (NCBI General Identification No. 1841475; SEQ ID NO: 63).

TABLE 6

Percent Identity of Amino Acid Sequences Deduced From the Nucleotide Sequences of cDNA Clones Encoding Polypeptides Homologous to Myb-related Transcription Factors

| SEQ ID NO. | Percent Identity to NCBI General Identification No. 1841475 |
|---|---|
| 10 | 43.8 |
| 14 | 33.2 |
| 26 | 30.9 |
| 30 | 75.6 |
| 32 | 74.1 |
| 34 | 64.1 |
| 36 | 77.7 |
| 42 | 43.8 |
| 44 | 48.5 |
| 46 | 46.5 |

TABLE 6-continued

Percent Identity of Amino Acid Sequences Deduced From the Nucleotide Sequences of cDNA Clones Encoding Polypeptides Homologous to Myb-related Transcription Factors

| SEQ ID NO. | Percent Identity to NCBI General Identification No. 1841475 |
|---|---|
| 48 | 45.6 |
| 50 | 46.1 |
| 54 | 31.8 |

Sequence alignments and percent identity calculations were performed using the Magalion program of the LASERGENE bioinformatics computing suite (DNASTAR Inc., Madison, Wis.) Multiple alignment of the sequences was performed using the Clustal method of alignment (Higgins and Sharp (1989) *CABIOS.* 5:151-153) with the default parameters (GAP LENGTH PENALTY=10). Default parameters for pairwise alignments using the Clustal method were KTUPLE 1, GAP PENALTY=3, WINDOWS=5 and DIAGONALS SAVED=5. Sequence alignments and BLAST scores and probabilities indicate that the nucleic acid fragments comprising the instant cDNA clones encode all or a substantial portion of a Myb-related transcription factor. These sequences represent the first soybean and wheat sequences encoding Myb-related transcription factors. Nucleic acid fragments encoding Myb-related transcription factors have previously been isolated from rice and corn (Marocco et al. (1989) *Mol Gen Genet.* 216:183-187; Pandolfi et al. (1997) *Plant Physiol* 114:747).

Example 4

Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptide, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) Sci. Sin. Peking 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35 S/Ac is under the control of 35S promoter from Cauliflower Mosaic Virus (Odell et al. (1985) Nature 313:810-812) and the 3' region of the nopaline synthase gene from the T-DNA of the Ti plasmid of Agrobacterium tumefaciens.

The particle bombardment method (Klein et al. (1987) Nature 327:70-73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833-839).

Example 5

Expression of Chimeric Genes in Dicot Cells

A seed-specific expression cassette composed of the promoter and transcription terminator from the gene encoding the β subunit of the seed storage protein phaseolin from the bean Phaseolus vulgaris (Doyle et al. (1986) J. Biol. Chem. 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810-812), the hygromycin phosphotransferase gene from plasmid pJR225 (from E. coli; Gritz et al.(1983) Gene 25:179-188) and the 3' region of the nopaline synthase gene from the T-DNA of the Ti plasmid of Agrobacterium tumefaciens. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 7

Assaying Myb-Related Transcription Factor Activity

The polypeptides described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a $(His)_6$ peptide may be engineered into the N-terminus of the fused thioredoxin moiety to afford additional opportunities for affinity purification. Other suitable affinity resins could be synthesized by linking the appropriate ligands to any suitable resin such as Sepharosetraditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays to verify over- or underexpression of functional Myb-related transcription factor protein in transgenic plants and transformed bacterial cells. Assays may be conducted under well known experimental conditions which permit optimal enzymatic activity. For example, assays for Myb-related transcription factors are presented by Moyano et al. (1996) *Plant Cell* 8:1519-1532.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

What is claimed is:

1. An isolated polypeptide comprising an amino acid sequence of at least 95% sequence identity when compared to SEQ ID NO: 36, based on the Clustal V method of alignment with pairwise alignment default parameters of KTUPLE=1, GAP PENALTY=3, WINDOW=5 and DIAGONALS SAVED=5, wherein the polypeptide has Myb-related transcription factor activity.

2. The isolated polypeptide of claim 1, wherein the amino acid sequence of the polypeptide comprises SEQ ID NO: 36.

3. An isolated fusion protein comprising a fusion protein partner covalently linked to the isolated polypeptide of claim 1.

4. The isolated fusion protein of claim 3, wherein the fusion protein partner is at least one selected from the group consisting of glutathione S-transferase, thioredoxin, maltose binding protein, and a hexahistidine polypeptide.

* * * * *

```
                         SEQUENCE LISTING

<160> NUMBER OF SEQ ID NOS: 63

<210> SEQ ID NO 1
<211> LENGTH: 771
<212> TYPE: DNA
<213> ORGANISM: Zea mays
<220> FEATURE:
<221> NAME/KEY: unsure
<222> LOCATION: (4)
<223> OTHER INFORMATION: n is a, c, g or t
<220> FEATURE:
<221> NAME/KEY: unsure
<222> LOCATION: (99)
<223> OTHER INFORMATION: n is a, c, g or t
<220> FEATURE:
<221> NAME/KEY: unsure
<222> LOCATION: (396)
<223> OTHER INFORMATION: n is a, c, g or t
<220> FEATURE:
<221> NAME/KEY: unsure
<222> LOCATION: (470)
<223> OTHER INFORMATION: n is a, c, g or t
<220> FEATURE:
<221> NAME/KEY: unsure
<222> LOCATION: (486)
<223> OTHER INFORMATION: n is a, c, g or t
<220> FEATURE:
<221> NAME/KEY: unsure
<222> LOCATION: (586)
<223> OTHER INFORMATION: n is a, c, g or t
<220> FEATURE:
<221> NAME/KEY: unsure
<222> LOCATION: (600)
<223> OTHER INFORMATION: n is a, c, g or t
<220> FEATURE:
<221> NAME/KEY: unsure
<222> LOCATION: (612)
<223> OTHER INFORMATION: n is a, c, g or t
<220> FEATURE:
<221> NAME/KEY: unsure
<222> LOCATION: (615)
<223> OTHER INFORMATION: n is a, c, g or t
<220> FEATURE:
<221> NAME/KEY: unsure
<222> LOCATION: (627)
<223> OTHER INFORMATION: n is a, c, g or t
<220> FEATURE:
<221> NAME/KEY: unsure
<222> LOCATION: (632)
<223> OTHER INFORMATION: n is a, c, g or t
<220> FEATURE:
<221> NAME/KEY: unsure
```

```
<222> LOCATION: (658)
<223> OTHER INFORMATION: n is a, c, g or t
<220> FEATURE:
<221> NAME/KEY: unsure
<222> LOCATION: (690)
<223> OTHER INFORMATION: n is a, c, g or t
<220> FEATURE:
<221> NAME/KEY: unsure
<222> LOCATION: (716)
<223> OTHER INFORMATION: n is a, c, g or t
<220> FEATURE:
<221> NAME/KEY: unsure
<222> LOCATION: (724)
<223> OTHER INFORMATION: n is a, c, g or t
<220> FEATURE:
<221> NAME/KEY: unsure
<222> LOCATION: (736)
<223> OTHER INFORMATION: n is a, c, g or t
<220> FEATURE:
<221> NAME/KEY: unsure
<222> LOCATION: (752)
<223> OTHER INFORMATION: n is a, c, g or t
<220> FEATURE:
<221> NAME/KEY: unsure
<222> LOCATION: (758)
<223> OTHER INFORMATION: n is a, c, g or t

<400> SEQUENCE: 1
caancgcggg attgttcaat ccgttcgaca tcacaaaatc cacgcacaaa gaagcgacag      60
atgactacga gcagggtggc caggtcgtgc ggccgcggna cgacgatga gccggcggtg     120
cgcaagggc cgtggacgct ggaggaggac ctcatcctcg tcagctacat ctcccagcac    180
ggggagggct cctgggacaa cctcgcgcgc gcagctggac tgaaccgcaa cggcaagagc    240
tgcaggctgc ggtggctcaa ctacctgagg ccgggggtgc ggcgcggcag catcacggcg    300
ggggaggaca cggtcatccg ggagctccac gcgaggtggg ggaacaagtg gtccaagatc    360
tccaagcacc tccccggccg aaccgacaac gagatnaaga actactggag gaccaggatc    420
caacaagaag aacagcaagg agccaagacg acgcaacaac gggaccgtcn acgaccgcca    480
actccngggc ccggggacga ctactggtg cacaacccga ccccgacaac aagccatact    540
gcctgcaaaa accccatgca actgcacgcg acaacaaccg gtctcntaac aacaagacan    600
cccttcggg gnctnacaac cagaaanccc cnccggcggg gaatggtaat cacaacanaa    660
attgtacct ctgtccaact aactttcccn cggcacataa acgtcggctg acctttacaa    720
tcantcttct ccactnatgc actttgcaac gngtgtantt tgataaacct t              771

<210> SEQ ID NO 2
<211> LENGTH: 157
<212> TYPE: PRT
<213> ORGANISM: Zea mays
<220> FEATURE:
<221> NAME/KEY: UNSURE
<222> LOCATION: (111)
<223> OTHER INFORMATION: Xaa can be any naturally occurring amino acid
<220> FEATURE:
<221> NAME/KEY: UNSURE
<222> LOCATION: (136)
<223> OTHER INFORMATION: Xaa can be any naturally occurring amino acid

<400> SEQUENCE: 2

Thr Thr Ser Arg Val Ala Arg Ser Cys Gly Arg Gly Ser Asp Asp Glu
  1               5                  10                  15

Pro Ala Val Arg Lys Gly Pro Trp Thr Leu Glu Glu Asp Leu Ile Leu
                 20                  25                  30

Val Ser Tyr Ile Ser Gln His Gly Glu Gly Ser Trp Asp Asn Leu Ala
             35                  40                  45
```

```
Arg Ala Ala Gly Leu Asn Arg Asn Gly Lys Ser Cys Arg Leu Arg Trp
     50                  55                  60
Leu Asn Tyr Leu Arg Pro Gly Val Arg Gly Ser Ile Thr Ala Gly
 65                  70                  75                  80
Glu Asp Thr Val Ile Arg Glu Leu His Ala Arg Trp Gly Asn Lys Trp
                     85                  90                  95
Ser Lys Ile Ser Lys His Leu Pro Gly Arg Thr Asp Asn Glu Xaa Lys
                100                 105                 110
Asn Tyr Trp Arg Thr Arg Ile Gln Gln Glu Glu Gln Gln Gly Ala Lys
            115                 120                 125
Thr Thr Gln Gln Arg Asp Arg Xaa Arg Pro Pro Thr Pro Gly Pro Gly
        130                 135                 140
Asp Asp Tyr Trp Val His Asn Pro Thr Pro Thr Ser
145                 150                 155

<210> SEQ ID NO 3
<211> LENGTH: 782
<212> TYPE: DNA
<213> ORGANISM: Zea mays
<220> FEATURE:
<221> NAME/KEY: unsure
<222> LOCATION: (3)
<223> OTHER INFORMATION: n is a, c, g or t

<400> SEQUENCE: 3
acngtctgct gcaggtacgg gccgtaatcc gggtcgacca cgcgtcccga caaagtggca        60
tactcttctc tgtactagct ttcttcttcc tctcctcttc ctcacaaaca gactggattt       120
caacaagata atcctgaaac tggagccaac aagcacacag agaaagaaga gcaagaagac       180
cggctcccag ccgatacaag gtaggagtga gcagcgttag tttcatcata tcgcataggc       240
gatatggtga cagtgagaga ggagactcgc aaggggccat ggacagagca ggaggacctg       300
caactggtat gcactgtccg tctgttcggt gaacgtcgtt gggatttcat tgccaaagta       360
tcaggactca accggacagg caagagctgc cggctgcggt gggtcaacta cctccaccct       420
ggcctcaagc gtgggcgcat gtctccccat gaagagcgcc tcatccttga gctgcacgct       480
cggtggggaa acaggtggtc caggatagca cggcgcttgc cagggcgcac tgacaatgag       540
atcaagaact actggaggac acacatgagg aagaaagcac aggagaggaa gaggaacatg       600
tctccatcat catcctcatc ttcactgagt taccagtcag gctacccaga tactccatca       660
atcattggag ttaagggaca ggagcttcat ggtggcagtg gctgcatcac aagcatcctg       720
aagggcaccc atccggacat ggatggctat cccatggacc agatatggat ggaattgaag       780
gg                                                                     782

<210> SEQ ID NO 4
<211> LENGTH: 179
<212> TYPE: PRT
<213> ORGANISM: Zea mays

<400> SEQUENCE: 4

Met Val Thr Val Arg Glu Glu Thr Arg Lys Gly Pro Trp Thr Glu Gln
  1               5                  10                  15
Glu Asp Leu Gln Leu Val Cys Thr Val Arg Leu Phe Gly Glu Arg Arg
                 20                  25                  30
Trp Asp Phe Ile Ala Lys Val Ser Gly Leu Asn Arg Thr Gly Lys Ser
             35                  40                  45
```

```
Cys Arg Leu Arg Trp Val Asn Tyr Leu His Pro Gly Leu Lys Arg Gly
 50                  55                  60
Arg Met Ser Pro His Glu Glu Arg Leu Ile Leu Glu Leu His Ala Arg
 65                  70                  75                  80
Trp Gly Asn Arg Trp Ser Arg Ile Ala Arg Arg Leu Pro Gly Arg Thr
                 85                  90                  95
Asp Asn Glu Ile Lys Asn Tyr Trp Arg Thr His Met Arg Lys Lys Ala
                100                 105                 110
Gln Glu Arg Lys Arg Asn Met Ser Pro Ser Ser Ser Ser Ser Ser Leu
                115                 120                 125
Ser Tyr Gln Ser Gly Tyr Pro Asp Thr Pro Ser Ile Ile Gly Val Lys
            130                 135                 140
Gly Gln Glu Leu His Gly Gly Ser Gly Cys Ile Thr Ser Ile Leu Lys
145                 150                 155                 160
Gly Thr His Pro Asp Met Asp Gly Tyr Pro Met Asp Gln Ile Trp Met
                165                 170                 175
Glu Leu Lys

<210> SEQ ID NO 5
<211> LENGTH: 601
<212> TYPE: DNA
<213> ORGANISM: Zea mays
<220> FEATURE:
<221> NAME/KEY: unsure
<222> LOCATION: (451)
<223> OTHER INFORMATION: n is a, c, g or t
<220> FEATURE:
<221> NAME/KEY: unsure
<222> LOCATION: (456)
<223> OTHER INFORMATION: n is a, c, g or t
<220> FEATURE:
<221> NAME/KEY: unsure
<222> LOCATION: (478)
<223> OTHER INFORMATION: n is a, c, g or t
<220> FEATURE:
<221> NAME/KEY: unsure
<222> LOCATION: (480)
<223> OTHER INFORMATION: n is a, c, g or t
<220> FEATURE:
<221> NAME/KEY: unsure
<222> LOCATION: (490)
<223> OTHER INFORMATION: n is a, c, g or t
<220> FEATURE:
<221> NAME/KEY: unsure
<222> LOCATION: (510)
<223> OTHER INFORMATION: n is a, c, g or t
<220> FEATURE:
<221> NAME/KEY: unsure
<222> LOCATION: (542)
<223> OTHER INFORMATION: n is a, c, g or t
<220> FEATURE:
<221> NAME/KEY: unsure
<222> LOCATION: (549)
<223> OTHER INFORMATION: n is a, c, g or t
<220> FEATURE:
<221> NAME/KEY: unsure
<222> LOCATION: (552)
<223> OTHER INFORMATION: n is a, c, g or t
<220> FEATURE:
<221> NAME/KEY: unsure
<222> LOCATION: (554)
<223> OTHER INFORMATION: n is a, c, g or t
<220> FEATURE:
<221> NAME/KEY: unsure
<222> LOCATION: (572)
<223> OTHER INFORMATION: n is a, c, g or t
<220> FEATURE:
<221> NAME/KEY: unsure
<222> LOCATION: (578)
<223> OTHER INFORMATION: n is a, c, g or t
```

```
<220> FEATURE:
<221> NAME/KEY: unsure
<222> LOCATION: (583)
<223> OTHER INFORMATION: n is a, c, g or t
<220> FEATURE:
<221> NAME/KEY: unsure
<222> LOCATION: (588)
<223> OTHER INFORMATION: n is a, c, g or t
<220> FEATURE:
<221> NAME/KEY: unsure
<222> LOCATION: (595)
<223> OTHER INFORMATION: n is a, c, g or t
<220> FEATURE:
<221> NAME/KEY: unsure
<222> LOCATION: (601)
<223> OTHER INFORMATION: n is a, c, g or t

<400> SEQUENCE: 5
aaccgccgat catcggctat acctaccagc tcgctgttct tgctgaagcc ctggagctat      60
atagcttcga tctgcgcagc acaggttgtc tgtcgactag tgattagtga agaagatggc     120
ggcgcgtgac caccgagagc tgagcggcga cgaggactcc gtggtggcgg ccggagacct     180
ccgccgcggg ccgtggacgg tggaggagga catgctcctc gtcaactacg tcgccgcgca     240
cggcgagggc cgctggaacg cgctggcacg atgcgcaggg ctccggcgga cggggaagag     300
ctgccgcctg cggtggctca actacctgcg gccggacctg cggcggggca acatcacggc     360
gcaagagcaa ctgctcatcc tggagctgca ctcccgctgg ggcaaccgct ggtcaagatc     420
gcgcagcacc tccaagggca acgacaacga natcanaact actggcgcac cggttcanan     480
cacccagcan ctcaatgcaa ctcaaagcan cgctcaagga ctcagcgcta atctggatgc     540
gngctcccna angnaccgtc gacatccggg angggctnct ttngagcnca cccancaaac     600 n                                                                    601

<210> SEQ ID NO 6
<211> LENGTH: 120
<212> TYPE: PRT
<213> ORGANISM: Zea mays
<220> FEATURE:
<221> NAME/KEY: UNSURE
<222> LOCATION: (101)
<223> OTHER INFORMATION: Xaa can be any naturally occurring amino acid
<220> FEATURE:
<221> NAME/KEY: UNSURE
<222> LOCATION: (113)..(114)
<223> OTHER INFORMATION: Xaa can be any naturally occurring amino acid

<400> SEQUENCE: 6

Met Ala Ala Arg Asp His Arg Glu Leu Ser Gly Asp Glu Asp Ser Val
1               5                   10                  15

Val Ala Ala Gly Asp Leu Arg Arg Gly Pro Trp Thr Val Glu Glu Asp
            20                  25                  30

Met Leu Leu Val Asn Tyr Val Ala Ala His Gly Glu Gly Arg Trp Asn
        35                  40                  45

Ala Leu Ala Arg Cys Ala Gly Leu Arg Arg Thr Gly Lys Ser Cys Arg
    50                  55                  60

Leu Arg Trp Leu Asn Tyr Leu Arg Pro Asp Leu Arg Arg Gly Asn Ile
65                  70                  75                  80

Thr Ala Gln Glu Gln Leu Leu Ile Leu Glu Leu His Ser Arg Trp Gly
                85                  90                  95

Asn Arg Trp Ser Xaa Ile Ala Gln His Leu Gln Gly Gln Arg Gln Arg
            100                 105                 110

Xaa Xaa Asn Tyr Trp Arg Thr Gly
```

```
<210> SEQ ID NO 7
<211> LENGTH: 547
<212> TYPE: DNA
<213> ORGANISM: Zea mays
<220> FEATURE:
<221> NAME/KEY: unsure
<222> LOCATION: (356)
<223> OTHER INFORMATION: n is a, c, g or t
<220> FEATURE:
<221> NAME/KEY: unsure
<222> LOCATION: (374)
<223> OTHER INFORMATION: n is a, c, g or t
<220> FEATURE:
<221> NAME/KEY: unsure
<222> LOCATION: (479)
<223> OTHER INFORMATION: n is a, c, g or t
<220> FEATURE:
<221> NAME/KEY: unsure
<222> LOCATION: (508)
<223> OTHER INFORMATION: n is a, c, g or t
<220> FEATURE:
<221> NAME/KEY: unsure
<222> LOCATION: (532)
<223> OTHER INFORMATION: n is a, c, g or t

<400> SEQUENCE: 7
ccgataccgg cctcaacgcc ctcttttttcc cagcctcaca accaattcct gtttcagtcg      60
atcgcagtta gcatggccac gacacagagc tgtcagagca ggagcagcgc ctgcagcaag     120
gctgctgctt gcttcccggc cgccgtagcg gtcgacgagg agcacggcca ccacagccac     180
cagctgaagg gaggagcgca ggaggaggct gagaacgaca ataataagcc ggagctccgg     240
cgtggcccct ggacggtaga cgaggacctc accctcgtca actacatcgc cgacaacggc     300
gagggtccct ggaacaacct cgcccgcgcc gccgggctga gcggacggg caaganctgc     360 cggctgcggt ggcncaacta cctccggccc gacgtgaagc gtgggaactt cagcgccgac     420
gagcagctgc tcatctcgac ctcacaccgc tgggcaacc gatgtcgaag atagcgcanc     480
acctgccggg aaggacggca acgagatnaa gaactactgg aggaccgggt gnataacacg     540
caagatc                                                               547

<210> SEQ ID NO 8
<211> LENGTH: 72
<212> TYPE: PRT
<213> ORGANISM: Zea mays
<220> FEATURE:
<221> NAME/KEY: UNSURE
<222> LOCATION: (42)
<223> OTHER INFORMATION: Xaa can be any naturally occurring amino acid
<220> FEATURE:
<221> NAME/KEY: UNSURE
<222> LOCATION: (48)
<223> OTHER INFORMATION: Xaa can be any naturally occurring amino acid

<400> SEQUENCE: 8

Glu Leu Arg Arg Gly Pro Trp Thr Val Asp Glu Asp Leu Thr Leu Val
 1               5                  10                  15

Asn Tyr Ile Ala Asp Asn Gly Glu Gly Pro Trp Asn Asn Leu Ala Arg
            20                  25                  30

Ala Ala Gly Leu Lys Arg Thr Gly Lys Xaa Cys Arg Leu Arg Trp Xaa
        35                  40                  45

Asn Tyr Leu Arg Pro Asp Val Lys Arg Gly Asn Phe Ser Ala Asp Glu
    50                  55                  60

Gln Leu Leu Ile Ser Thr Ser His
```

<210> SEQ ID NO 9
<211> LENGTH: 1317
<212> TYPE: DNA
<213> ORGANISM: Zea mays

<400> SEQUENCE: 9

```
gcacgagccg ataccggcct caacgccctc tttttcccag cctcacaacc aattcctgtt      60
tcagtcgatc gcagttagca tggccacgac acagagctgt cagagcagga gcagcgcctg     120
cagcaaggct gctgcttgct tcccggccgc cgtagcggtc gacgaggagc acggccacca     180
cagccaccag ctgaagggag gagcgcagga ggaggctgag aacgacaata taagccgga     240
gctccggcgt ggcccctgga cggtagacga ggacctcacc ctcgtcaact acatcgccga    300
caacggcgag ggtcgctgga caacctcgc ccgcgccgcc gggctgaagc ggacgggcaa     360
gagctgccgc ctgcggtggc tcaactacct ccggcccgac gtgaagcgtg caacttcag     420
cgccgacgag cagctgctca tcctcgacct ccacacccgc tggggcaacc gatggtcgaa    480
gatagcgcag cacctgccgg gaaggacgga caacgagatc aagaactact ggaggacccg    540
ggtgcagaag cacgccaagc agctcaactg cgacgccaac agcaagcgct tcaaggacgc    600
catgcgctac ctctggatgc cgcacctcgc cgacgacgtc gataccatcg ctgcggccaa    660
cgacgacgac gaagaccacc accacaacct acgcctcctc gtcctgcacc accaccaggc    720
ccagcacctg cagcaagctg ctgccgcggc cggcggcgct gccaacgacc ttgctgcggg    780
cgcctacgac gtccgccagc tgcacgcgct gccgtcgtcg ggcatggcgg cgacgtcgtc    840
gtccgactcg ctcgcgtcgg agtcgtacga tgacggaggc ctgcttttcg cgaacttgcg    900
cgccggcgag atgctgatgg acggcggaga ttgggcggcg cagcaggagg ccgaccaagg    960
gctgtggccg ccgccgccgc cgccgccgtc tgatcttgat cagtcggtgg tgcaggctgc   1020
tggtgccggc gctggccagt tcaggacat ggagctcagt ggttgggtgc aaggcttctc    1080
cgagagcatt acagataact tttgggcctt ggaggaaatt tggaagatgc aatgagcgag   1140
caattttaca tcttacacat ccatccaaat taaagacaac atagatacac atatacatat   1200
catatattct aacaacaggt gccatatacg atatacatac acaagttgtt gtatagttgt   1260
attccgctta tatatatatt tttttgcct ctcaaaaaaa aaaaaaaaa aaaaaaa        1317
```

<210> SEQ ID NO 10
<211> LENGTH: 351
<212> TYPE: PRT
<213> ORGANISM: Zea mays

<400> SEQUENCE: 10

```
Met Ala Thr Thr Gln Ser Cys Gln Ser Arg Ser Ala Cys Ser Lys
 1               5                  10                  15

Ala Ala Ala Cys Phe Pro Ala Val Ala Val Asp Glu Glu His Gly
                20                  25                  30

His His Ser His Gln Leu Lys Gly Gly Ala Gln Glu Glu Ala Glu Asn
        35                  40                  45

Asp Asn Asn Lys Pro Glu Leu Arg Arg Gly Pro Trp Thr Val Asp Glu
    50                  55                  60

Asp Leu Thr Leu Val Asn Tyr Ile Ala Asp Asn Gly Glu Gly Arg Trp
65                  70                  75                  80

Asn Asn Leu Ala Arg Ala Ala Gly Leu Lys Arg Thr Gly Lys Ser Cys
                85                  90                  95
```

-continued

```
Arg Leu Arg Trp Leu Asn Tyr Leu Arg Pro Asp Val Lys Arg Gly Asn
            100                 105                 110

Phe Ser Ala Asp Glu Gln Leu Leu Ile Leu Asp Leu His Thr Arg Trp
        115                 120                 125

Gly Asn Arg Trp Ser Lys Ile Ala Gln His Leu Pro Gly Arg Thr Asp
    130                 135                 140

Asn Glu Ile Lys Asn Tyr Trp Arg Thr Arg Val Gln Lys His Ala Lys
145                 150                 155                 160

Gln Leu Asn Cys Asp Ala Asn Ser Lys Arg Phe Lys Asp Ala Met Arg
                165                 170                 175

Tyr Leu Trp Met Pro His Leu Ala Asp Asp Val Asp Thr Ile Ala Ala
            180                 185                 190

Ala Asn Asp Asp Glu Asp His His Asn Leu Arg Leu Leu Val
        195                 200                 205

Leu His His His Gln Ala Gln His Leu Gln Gln Ala Ala Ala Ala
    210                 215                 220

Gly Gly Ala Ala Asn Asp Leu Ala Ala Gly Ala Tyr Asp Val Arg Gln
225                 230                 235                 240

Leu His Ala Leu Pro Ser Ser Gly Met Ala Ala Thr Ser Ser Ser Asp
                245                 250                 255

Ser Leu Ala Ser Glu Ser Tyr Asp Asp Gly Gly Leu Leu Phe Ala Asn
            260                 265                 270

Leu Arg Ala Gly Glu Met Leu Met Asp Gly Asp Trp Ala Ala Gln
        275                 280                 285

Gln Glu Ala Asp Gln Gly Leu Trp Pro Pro Pro Pro Pro Pro Ser
    290                 295                 300

Asp Leu Asp Gln Ser Val Val Gln Ala Ala Gly Ala Gly Ala Gly Gln
305                 310                 315                 320

Phe Gln Asp Met Glu Leu Ser Gly Trp Val Gln Gly Phe Ser Glu Ser
                325                 330                 335

Ile Thr Asp Asn Phe Trp Ala Leu Glu Glu Ile Trp Lys Met Gln
            340                 345                 350

<210> SEQ ID NO 11
<211> LENGTH: 488
<212> TYPE: DNA
<213> ORGANISM: Oryza sativa

<400> SEQUENCE: 11
ggttcgtgcg gctgctgggc gaacggcggt gggatttctt agcaaaggtg tcaggtttgc      60
gcggcggcgg gtgatgagca tatgcgtgcg tgcatctaat ctatcgatta attgttgatg     120
atgtcgatca gatggatgga tgcatgcata tgccgtacat agtagatttg atgatagtaa     180
ctgacataaa tataatgtat gcgtgcgatc aacgctggtt gttggatcgt ccgtcgtgtg     240
tatgggtggt gtgtggctga tgcaggtttg cagcgcagcg ggaagagctg ccgtctccgg     300
tgggtgaact acctgcatcc agggctgaag cgagggagga tgagccccga ggaggagagg     360
atggtggtgc agctccacgc caagctcggc aacaggtggt ctcgcatcgc caagagcatt     420
cctggccgca ccgacaacga gatcaagaac tactggcgca cccacctgcg caagctcaag     480
ctcaaaca                                                              488

<210> SEQ ID NO 12
<211> LENGTH: 71
<212> TYPE: PRT
```

<213> ORGANISM: Oryza sativa

<400> SEQUENCE: 12

```
Val Tyr Gly Trp Cys Val Ala Asp Ala Gly Leu Gln Arg Ser Gly Lys
 1               5                  10                  15

Ser Cys Arg Leu Arg Trp Val Asn Tyr Leu His Pro Gly Leu Lys Arg
            20                  25                  30

Gly Arg Met Ser Pro Glu Glu Arg Met Val Gln Leu His Ala
        35                  40                  45

Lys Leu Gly Asn Arg Trp Ser Arg Ile Ala Lys Ser Ile Pro Gly Arg
    50                  55                  60

Thr Asp Asn Glu Ile Lys Asn
65                  70
```

<210> SEQ ID NO 13
<211> LENGTH: 1123
<212> TYPE: DNA
<213> ORGANISM: Oryza sativa

<400> SEQUENCE: 13

| | | |
|---|---|---|
| gcattctttt tctgcatcat catcgtcgtc ttcgtcttct tcttgttcag tagtgcagct | 60 |
| gggtcatcat cagcgcccac agggtgagga ccctctcatc ggcatcaaag cagcagcagc | 120 |
| aggaggagga ggaataatga gaaagggccc gtggacggag caggaggacg tgcagttggt | 180 |
| ttggttcgtg cggctgctgg gcgaacggcg gtgggatttc ttagcaaagg tgtcaggttt | 240 |
| gcagcgcagc gggaagagct gccgtctccg gtgggtgaac tacctgcatc cagggctgaa | 300 |
| gcgagggagg atgagccccg aggaggagag gatggtggtg cagctccacg ccaagctcgg | 360 |
| caacaggtgg tctcgcatcg ccaagagcat tcctggccgc accgacaacg agatcaagaa | 420 |
| ctactggcgc acccacctgc gcaagctcaa gctcaaacag caaaagcagc agcagtccga | 480 |
| cgaccaccac aacgacaacg acgacgacga cgaccgcaac tcctcctcct cttcgtcctc | 540 |
| ctccaacagc aacagcaacc tgcagcagca gccgcagcca gaggatgagt cgtcggccag | 600 |
| tggcagcctg caggcccaac atcatgagga ccagcaccaa ctgttccttc atcctctctg | 660 |
| gaacgacgac atcatcgtcg acgtcgactg ctggagcagc agcaccaacg tcgtcgctcc | 720 |
| gccgccgatg cccgcctcgc cgctctggga tatcgatgac gccttcttct gctcggatta | 780 |
| ttcgctacct ctctggggat agtatatatc atccatcagc cgccaagacg atgacgacta | 840 |
| catcaactcg atcgatcgat gcctcctaat catgtgggag tactcagctc atctcaattg | 900 |
| ttacatcctt gctacagctg ctaattactg taattactag cttgcatata gggatcgacg | 960 |
| gaggaattaa tatatacatg ttagtaactc gttctatagc gcaacttgca gttgcatctc | 1020 |
| aatctctgat cagtactata taaatatata tatatatgta acagctgcta gctatagcta | 1080 |
| gctgcgtaca catccatatg aatgtgtgtg tgttcatgct aaa | 1123 |

<210> SEQ ID NO 14
<211> LENGTH: 221
<212> TYPE: PRT
<213> ORGANISM: Oryza sativa

<400> SEQUENCE: 14

```
Met Arg Lys Gly Pro Trp Thr Glu Gln Glu Asp Val Gln Leu Val Trp
 1               5                  10                  15

Phe Val Arg Leu Leu Gly Glu Arg Arg Trp Asp Phe Leu Ala Lys Val
            20                  25                  30
```

```
Ser Gly Leu Gln Arg Ser Gly Lys Ser Cys Arg Leu Arg Trp Val Asn
        35                  40                  45

Tyr Leu His Pro Gly Leu Lys Arg Gly Arg Met Ser Pro Glu Glu Glu
    50                  55                  60

Arg Met Val Val Gln Leu His Ala Lys Leu Gly Asn Arg Trp Ser Arg
 65                  70                  75                  80

Ile Ala Lys Ser Ile Pro Gly Arg Thr Asp Asn Glu Ile Lys Asn Tyr
                85                  90                  95

Trp Arg Thr His Leu Arg Lys Leu Lys Leu Lys Gln Gln Lys Gln Gln
                    100                 105                 110

Gln Ser Asp Asp His His Asn Asp Asn Asp Asp Asp Asp Arg Asn
            115                 120                 125

Ser Ser Ser Ser Ser Ser Ser Asn Ser Asn Ser Asn Leu Gln Gln
        130                 135                 140

Gln Pro Gln Pro Glu Asp Glu Ser Ser Ala Ser Gly Ser Leu Gln Ala
145                 150                 155                 160

Gln His His Glu Asp Gln His Gln Leu Phe Leu His Pro Leu Trp Asn
                165                 170                 175

Asp Asp Ile Ile Val Asp Val Asp Cys Trp Ser Ser Thr Asn Val
                180                 185                 190

Val Ala Pro Pro Pro Met Pro Ala Ser Pro Leu Trp Asp Ile Asp Asp
                195                 200                 205

Ala Phe Phe Cys Ser Asp Tyr Ser Leu Pro Leu Trp Gly
        210                 215                 220
```

<210> SEQ ID NO 15
<211> LENGTH: 336
<212> TYPE: DNA
<213> ORGANISM: Oryza sativa
<220> FEATURE:
<221> NAME/KEY: unsure
<222> LOCATION: (308)
<223> OTHER INFORMATION: n is a, c, g or t
<400> SEQUENCE: 15

```
tctggagttg atcaaggctc taaacgtgaa gctggagcca acaaactcaa agaggaagaa      60
gaacacggag agtggctccc atcctatcca aggtaagaag tgaacaacgt tagcattgca     120
acatcccaag ccccaatatg gtgacagtga gagaggagat gcgcaaggga ccatggacag     180
agcaggagga cctgcaactg gtatgcactg tccgcctgtt cggtgaccgc cgttgggatt     240
tcgttgccaa agtatcaggt ttgaggggc tcaataggac aggcaagagc tgccgcctcc      300
gttgggtnaa ctaactccaa ccctgggcct caagca                               336
```

<210> SEQ ID NO 16
<211> LENGTH: 62
<212> TYPE: PRT
<213> ORGANISM: Oryza sativa
<220> FEATURE:
<221> NAME/KEY: UNSURE
<222> LOCATION: (59)
<223> OTHER INFORMATION: Xaa can be any naturally occurring amino acid
<400> SEQUENCE: 16

```
Met Val Thr Val Arg Glu Glu Met Arg Lys Gly Pro Trp Thr Glu Gln
  1               5                  10                  15

Glu Asp Leu Gln Leu Val Cys Thr Val Arg Leu Phe Gly Asp Arg Arg
                20                  25                  30

Trp Asp Phe Val Ala Lys Val Ser Gly Leu Arg Gly Leu Asn Arg Thr
```

```
                 35                  40                  45
Gly Lys Ser Cys Arg Leu Arg Trp Val Asn Xaa Leu Gln Pro
     50                  55                  60

<210> SEQ ID NO 17
<211> LENGTH: 587
<212> TYPE: DNA
<213> ORGANISM: Oryza sativa
<220> FEATURE:
<221> NAME/KEY: unsure
<222> LOCATION: (577)
<223> OTHER INFORMATION: n is a, c, g or t
<220> FEATURE:
<221> NAME/KEY: unsure
<222> LOCATION: (582)..(583)
<223> OTHER INFORMATION: n is a, c, g or t
<220> FEATURE:
<221> NAME/KEY: unsure
<222> LOCATION: (587)
<223> OTHER INFORMATION: n is a, c, g or t

<400> SEQUENCE: 17
ctctactaca cacttgctct gcccgatgat gatggcgcga gaggtgagca gcgaggagga      60
ggctggcggc ggcgacgagc tccggcgagg gccgtggacg gtggaggagg acctgctcct     120
cgtcaactac atcgccgccc atggcgaggg ccgctggaac gcgctcgcgc gctgcgccgg     180
gctgaagcgg acggggaaga gctgccggct gcggtggctg aactacctga ggccggacgt     240
gaggaggggg aacatgacgg cggaggagca gctgctgata ctggagctcc atgggcggtg     300
ggggaatcgg tggagcaaga tcgcgcagca tctccccggc cgcaccgaca cgagatcaa      360 gaactactgg cgcacccgcg tccagaagca cgccaagcac ctcaactgcg acgtcaactc     420
ccagcagttc aaggacctca tgcgctacct ctggatgccc gcctcctcga acgcatcaac     480
gctcctccca atccaatcca cgaccgacg acccgactct cgtctccgcc gcacactgat      540
cactcgactc tctcacgcca taacgccgct cgcatgncga annacan                   587
```

<210> SEQ ID NO 18
<211> LENGTH: 145
<212> TYPE: PRT
<213> ORGANISM: Oryza sativa

<400> SEQUENCE: 18

```
Met Met Met Ala Arg Glu Val Ser Ser Glu Glu Ala Gly Gly Gly
 1               5                  10                  15

Asp Glu Leu Arg Arg Gly Pro Trp Thr Val Glu Asp Leu Leu Leu
             20                  25                  30

Val Asn Tyr Ile Ala Ala His Gly Glu Gly Arg Trp Asn Ala Leu Ala
             35                  40                  45

Arg Cys Ala Gly Leu Lys Arg Thr Gly Lys Ser Cys Arg Leu Arg Trp
     50                  55                  60

Leu Asn Tyr Leu Arg Pro Asp Val Arg Arg Gly Asn Met Thr Ala Glu
 65                  70                  75                  80

Glu Gln Leu Leu Ile Leu Glu Leu His Gly Arg Trp Gly Asn Arg Trp
                 85                  90                  95

Ser Lys Ile Ala Gln His Leu Pro Gly Arg Thr Asp Asn Glu Ile Lys
            100                 105                 110

Asn Tyr Trp Arg Thr Arg Val Gln Lys His Ala Lys His Leu Asn Cys
            115                 120                 125

Asp Val Asn Ser Gln Gln Phe Lys Asp Leu Met Arg Tyr Leu Trp Met
        130                 135                 140
```

<210> SEQ ID NO 19
<211> LENGTH: 440
<212> TYPE: DNA
<213> ORGANISM: Oryza sativa

<400> SEQUENCE: 19

```
gccgccggtc tgaagaggac tgggaagagc tgccggctcc ggtggctgaa ctatctccgg      60
ccggatgtga agcgcggcaa cttcaccgca gaggagcagc tgctcatcct cgacctccac    120
tcccgatggg gcaaccgatg gtccaagata gcacaacatt tgcctgggag gaccgacgac    180
gagatcaaga actactggag gaccagagtg caaaagcatg ccaagcaact caattgtgat    240
gtcaacagca agaggttcaa ggatgccatg aagtacctat ggatgcctcg ccttgccgag    300
cgcatccatg ccagggctgg cgctgttgat gatagcggag actacagcaa caacgactta    360
tcatgtgtat ctggtgtaac aatggccact gttgctaatt gttttgatgg ctctccgagc    420
atggtgacta gctcatcctc                                                  440
```

<210> SEQ ID NO 20
<211> LENGTH: 146
<212> TYPE: PRT
<213> ORGANISM: Oryza sativa

<400> SEQUENCE: 20

```
Ala Ala Gly Leu Lys Arg Thr Gly Lys Ser Cys Arg Leu Arg Trp Leu
  1               5                  10                  15

Asn Tyr Leu Arg Pro Asp Val Lys Arg Gly Asn Phe Thr Ala Glu Glu
             20                  25                  30

Gln Leu Leu Ile Leu Asp Leu His Ser Arg Trp Gly Asn Arg Trp Ser
         35                  40                  45

Lys Ile Ala Gln His Leu Pro Gly Arg Thr Asp Asp Glu Ile Lys Asn
     50                  55                  60

Tyr Trp Arg Thr Arg Val Gln Lys His Ala Lys Gln Leu Asn Cys Asp
 65                  70                  75                  80

Val Asn Ser Lys Arg Phe Lys Asp Ala Met Lys Tyr Leu Trp Met Pro
                 85                  90                  95

Arg Leu Ala Glu Arg Ile His Ala Arg Ala Gly Ala Val Asp Asp Ser
            100                 105                 110

Gly Asp Tyr Ser Asn Asn Asp Leu Ser Cys Val Ser Gly Val Thr Met
        115                 120                 125

Ala Thr Val Ala Asn Cys Phe Asp Gly Ser Pro Ser Met Val Thr Ser
    130                 135                 140

Ser Ser
145
```

<210> SEQ ID NO 21
<211> LENGTH: 640
<212> TYPE: DNA
<213> ORGANISM: Oryza sativa
<220> FEATURE:
<221> NAME/KEY: unsure
<222> LOCATION: (355)
<223> OTHER INFORMATION: n is a, c, g or t
<220> FEATURE:
<221> NAME/KEY: unsure
<222> LOCATION: (498)
<223> OTHER INFORMATION: n is a, c, g or t
<220> FEATURE:
<221> NAME/KEY: unsure
<222> LOCATION: (534)
<223> OTHER INFORMATION: n is a, c, g or t
<220> FEATURE:
<221> NAME/KEY: unsure
<222> LOCATION: (543)
<223> OTHER INFORMATION: n is a, c, g or t
<220> FEATURE:
<221> NAME/KEY: unsure
<222> LOCATION: (582)
<223> OTHER INFORMATION: n is a, c, g or t
<220> FEATURE:
<221> NAME/KEY: unsure
<222> LOCATION: (597)
<223> OTHER INFORMATION: n is a, c, g or t
<220> FEATURE:
<221> NAME/KEY: unsure
<222> LOCATION: (606)
<223> OTHER INFORMATION: n is a, c, g or t
<220> FEATURE:
<221> NAME/KEY: unsure
<222> LOCATION: (619)
<223> OTHER INFORMATION: n is a, c, g or t
<220> FEATURE:
<221> NAME/KEY: unsure
<222> LOCATION: (634)
<223> OTHER INFORMATION: n is a, c, g or t

<400> SEQUENCE: 21

```
ggcgtacatc catccatcca tccatctatc cagagagcac agcaacggcg catatatagt    60
acccctctac caaagcacaa caaccagaat ctcctgagct cgatctagct actagcttga   120
tctatccgat caatcgactg gcccgcgagg atcgatcgag actcgaaagg gagggatttt   180
gatccggatc ggtcgacgat ggacatggcg cacgagaggg acgcgagcag cgaggaggag   240
gtgatgggcg gcgacctgcg tcgcgggccg tggacggtgg aggaggacct cctgctcgtc   300
aactacatcg ccgcgcacgg cgagggccgc tggaactcgc tcgcccgatc agcanggctg   360
aaacgcacag gcaagagctg ccggctccgg tggctgaact acctccgccc cgacctccgg   420
cgaggcaaca tcacgccgca agagcagctg ctcatcctgg agctgcactc gcggtgggga   480
aaccgctggt ccaagatngc gcagcacctc ccgggaagca ccgacaacga gatnaagaat   540
acnggcgcac gcggtgcaga agcacccaag cagtcaagtg cnactcaaca gcaacantta   600
aggacncatg cgctactcng gatgcccgct cttnagggat                         640
```

<210> SEQ ID NO 22
<211> LENGTH: 115
<212> TYPE: PRT
<213> ORGANISM: Oryza sativa
<220> FEATURE:
<221> NAME/KEY: UNSURE
<222> LOCATION: (53)
<223> OTHER INFORMATION: Xaa can be any naturally occurring amino acid
<220> FEATURE:
<221> NAME/KEY: UNSURE
<222> LOCATION: (100)
<223> OTHER INFORMATION: Xaa can be any naturally occurring amino acid
<220> FEATURE:
<221> NAME/KEY: UNSURE
<222> LOCATION: (112)
<223> OTHER INFORMATION: Xaa can be any naturally occurring amino acid

<400> SEQUENCE: 22

```
Met Asp Met Ala His Glu Arg Asp Ala Ser Ser Glu Glu Glu Val Met
  1               5                  10                  15

Gly Gly Asp Leu Arg Arg Gly Pro Trp Thr Val Glu Glu Asp Leu Leu
             20                  25                  30
```

```
Leu Val Asn Tyr Ile Ala Ala His Gly Glu Gly Arg Trp Asn Ser Leu
            35                  40                  45

Ala Arg Ser Ala Xaa Leu Lys Arg Thr Gly Lys Ser Cys Arg Leu Arg
 50                  55                  60

Trp Leu Asn Tyr Leu Arg Pro Asp Leu Arg Arg Gly Asn Ile Thr Pro
 65                  70                  75                  80

Gln Glu Gln Leu Leu Ile Leu Glu Leu His Ser Arg Trp Gly Asn Arg
                 85                  90                  95

Trp Ser Lys Xaa Ala Gln His Leu Pro Gly Ser Thr Asp Asn Glu Xaa
            100                 105                 110

Lys Asn Thr
        115

<210> SEQ ID NO 23
<211> LENGTH: 484
<212> TYPE: DNA
<213> ORGANISM: Oryza sativa
<220> FEATURE:
<221> NAME/KEY: unsure
<222> LOCATION: (118)
<223> OTHER INFORMATION: n is a, c, g or t
<220> FEATURE:
<221> NAME/KEY: unsure
<222> LOCATION: (298)
<223> OTHER INFORMATION: n is a, c, g or t
<220> FEATURE:
<221> NAME/KEY: unsure
<222> LOCATION: (355)..(356)
<223> OTHER INFORMATION: n is a, c, g or t
<220> FEATURE:
<221> NAME/KEY: unsure
<222> LOCATION: (374)
<223> OTHER INFORMATION: n is a, c, g or t
<220> FEATURE:
<221> NAME/KEY: unsure
<222> LOCATION: (376)
<223> OTHER INFORMATION: n is a, c, g or t
<220> FEATURE:
<221> NAME/KEY: unsure
<222> LOCATION: (381)
<223> OTHER INFORMATION: n is a, c, g or t
<220> FEATURE:
<221> NAME/KEY: unsure
<222> LOCATION: (386)
<223> OTHER INFORMATION: n is a, c, g or t
<220> FEATURE:
<221> NAME/KEY: unsure
<222> LOCATION: (393)
<223> OTHER INFORMATION: n is a, c, g or t
<220> FEATURE:
<221> NAME/KEY: unsure
<222> LOCATION: (408)..(409)
<223> OTHER INFORMATION: n is a, c, g or t
<220> FEATURE:
<221> NAME/KEY: unsure
<222> LOCATION: (417)
<223> OTHER INFORMATION: n is a, c, g or t
<220> FEATURE:
<221> NAME/KEY: unsure
<222> LOCATION: (432)
<223> OTHER INFORMATION: n is a, c, g or t
<220> FEATURE:
<221> NAME/KEY: unsure
<222> LOCATION: (453)
<223> OTHER INFORMATION: n is a, c, g or t
<220> FEATURE:
<221> NAME/KEY: unsure
<222> LOCATION: (466)
<223> OTHER INFORMATION: n is a, c, g or t
<220> FEATURE:
<221> NAME/KEY: unsure
<222> LOCATION: (469)
<223> OTHER INFORMATION: n is a, c, g or t
```

```
<220> FEATURE:
<221> NAME/KEY: unsure
<222> LOCATION: (476)..(477)
<223> OTHER INFORMATION: n is a, c, g or t

<400> SEQUENCE: 23
cttacacctg atcgagatcg agtagtagtg acacgcatac accaccaacc accgccgccc    60
gccgccggcg agctgcagga tggggaggcc gccgtgctgc gacaaggtcg gggtgaanaa   120
ggggccatgg acgccggagg aggacctgat gctggtctcc tacatccagg agcacggcgc   180
cggcaactgg cgcgccgtgc cgacgaacac cgggctgatg cgttgcagca agagctgccg   240
gctccggtgg acgaactacc tcaggccggg gatcaagcgg gggaacttca ccgagcanga   300
ggagaagctc atcgtccacc tccaggctct cctcggcaac cggtgggcaa cgatnncgtc   360
gtacttgccg gganangacg ncaacnacat cangaatact gggaacannc acctcangaa   420
gaactcaaga anatgcaagc caccggaggt ggngaaaaca gcgcgncgnc tcggann gtt   480 gcgg                                                                484

<210> SEQ ID NO 24
<211> LENGTH: 126
<212> TYPE: PRT
<213> ORGANISM: Oryza sativa
<220> FEATURE:
<221> NAME/KEY: UNSURE
<222> LOCATION: (13)
<223> OTHER INFORMATION: Xaa can be any naturally occurring amino acid
<220> FEATURE:
<221> NAME/KEY: UNSURE
<222> LOCATION: (73)
<223> OTHER INFORMATION: Xaa can be any naturally occurring amino acid
<220> FEATURE:
<221> NAME/KEY: UNSURE
<222> LOCATION: (92)..(93)
<223> OTHER INFORMATION: Xaa can be any naturally occurring amino acid
<220> FEATURE:
<221> NAME/KEY: UNSURE
<222> LOCATION: (99)
<223> OTHER INFORMATION: Xaa can be any naturally occurring amino acid
<220> FEATURE:
<221> NAME/KEY: UNSURE
<222> LOCATION: (101)
<223> OTHER INFORMATION: Xaa can be any naturally occurring amino acid
<220> FEATURE:
<221> NAME/KEY: UNSURE
<222> LOCATION: (103)
<223> OTHER INFORMATION: Xaa can be any naturally occurring amino acid
<220> FEATURE:
<221> NAME/KEY: UNSURE
<222> LOCATION: (105)
<223> OTHER INFORMATION: Xaa can be any naturally occurring amino acid
<220> FEATURE:
<221> NAME/KEY: UNSURE
<222> LOCATION: (110)
<223> OTHER INFORMATION: Xaa can be any naturally occurring amino acid
<220> FEATURE:
<221> NAME/KEY: UNSURE
<222> LOCATION: (113)
<223> OTHER INFORMATION: Xaa can be any naturally occurring amino acid
<220> FEATURE:
<221> NAME/KEY: UNSURE
<222> LOCATION: (118)
<223> OTHER INFORMATION: Xaa can be any naturally occurring amino acid
<220> FEATURE:
<221> NAME/KEY: UNSURE
<222> LOCATION: (125)
<223> OTHER INFORMATION: Xaa can be any naturally occurring amino acid

<400> SEQUENCE: 24

Met Gly Arg Pro Pro Cys Cys Asp Lys Val Gly Val Xaa Lys Gly Pro
 1               5                  10                  15
```

```
Trp Thr Pro Glu Glu Asp Leu Met Leu Val Ser Tyr Ile Gln Glu His
         20                  25                  30
Gly Ala Gly Asn Trp Arg Ala Val Pro Thr Asn Thr Gly Leu Met Arg
     35                  40                  45
Cys Ser Lys Ser Cys Arg Leu Arg Trp Thr Asn Tyr Leu Arg Pro Gly
 50                  55                  60
Ile Lys Arg Gly Asn Phe Thr Glu Xaa Glu Lys Leu Ile Val His
 65                  70                  75                  80
Leu Gln Ala Leu Leu Gly Asn Arg Trp Ala Thr Xaa Xaa Ser Tyr Leu
                 85                  90                  95
Pro Gly Xaa Asp Xaa Asn Xaa Ile Xaa Asn Thr Gly Asn Xaa His Leu
             100                 105                 110
Xaa Lys Asn Ser Arg Xaa Cys Lys Pro Pro Glu Val Xaa Lys
         115                 120                 125
```

<210> SEQ ID NO 25
<211> LENGTH: 1427
<212> TYPE: DNA
<213> ORGANISM: Oryza sativa

<400> SEQUENCE: 25

```
gcacgagctt acacctgatc gagatcgagt agtagtgaca cgcatacacc accaaccacc    60
gccgcccgcc gccggcgagc tgcaggatgg ggaggccgcc gtgctgcgac aaggtcgggg   120
tgaagaaggg gccatggacg ccggaggagg acctgatgct ggtctcctac atccaggagc   180
acggcgccgg caactggcgc gccgtgccga cgaacaccgg gctgatgcgt tgcagcaaga   240
gctgccggct ccggtggacg aactacctca ggccggggat caagcggggg aacttcaccg   300
agcaggagga gaagctcatc gtccacctcc aggctctcct cggcaaccgg tgggcagcga   360
tagcgtcgta cttgccggag aggacggaca acgacatcaa gaactactgg aacacgcacc   420
tcaagaagaa gctcaagaag atgcaggccg ccggaggtgg ggaagacagc ggcgccgcct   480
cggagggtgg cggcggccgc ggcgacggcg acggcggcgg gaaaagcgtg aaggccgccg   540
cacctaaggg gcagtgggag cggcggctgc agacggacat ccacacggcg cggcaggcgc   600
tgcgcgacgc gctctcgctc gaccaccccg acccgtcgcc ggcgacggcg cggcggcgg   660
cgacgccagc ggggtcgtcg gcggcgtacg cgtcgagcgc ggacaacatc gcgcggctgc   720
tgcagggctg gatgcgcccg gcggcggcgg cggcggcaa cggcaagggc cccgaggcgt   780
cggggtcgac ctccacgacg gcgacgacgc agcagcagcc gcagtgctcc ggcgagggcg   840
cggcatccgc gtccgcgtcg gcgagccaga gcggcgccgc cgccgcggcg actgcccaga   900
cgccggagtg ctcgacggag acgagcaaga tggccaccgg cggcggcgcc ggcggccccg   960
cgccggcgtt ctcgatgctg agagctggc tgctcgacga cggcggcatg gggctcatgg  1020
acgtggtgcc attgggggac cccagtgagt tcttttaagt gtagtacaac caaaattaaa  1080
ttaatcaagt agacagcaag aacaaaaaaa aataatggaa agttgccgag ttaattaatc  1140
aagatgcaac taatcaaagc taattaaaag ggcttcgagt taattctcgg tgatttaaat  1200
cgagtttgca ggtgttgatc tagcttggtt aattaatcct ttcttttgta ggttttagt   1260
taattagtct ctctgatgat gctagggttt ggaactgatc atatgtaagt taatttatac  1320
taatggtagg cctgtgactt gtgattagtt agtcctgagt ggataaataa agacataaat  1380
gtacatcttt ttaaaagata aaaaaaaaaa aaaaaaaaa aaaaaaa                  1427
```

```
<210> SEQ ID NO 26
<211> LENGTH: 323
<212> TYPE: PRT
<213> ORGANISM: Oryza sativa

<400> SEQUENCE: 26

Met Gly Arg Pro Pro Cys Cys Asp Lys Val Gly Val Lys Lys Gly Pro
1               5                   10                  15

Trp Thr Pro Glu Glu Asp Leu Met Leu Val Ser Tyr Ile Gln Glu His
            20                  25                  30

Gly Ala Gly Asn Trp Arg Ala Val Pro Thr Asn Thr Gly Leu Met Arg
        35                  40                  45

Cys Ser Lys Ser Cys Arg Leu Arg Trp Thr Asn Tyr Leu Arg Pro Gly
    50                  55                  60

Ile Lys Arg Gly Asn Phe Thr Glu Gln Glu Lys Leu Ile Val His
65                  70                  75                  80

Leu Gln Ala Leu Leu Gly Asn Arg Trp Ala Ala Ile Ala Ser Tyr Leu
                85                  90                  95

Pro Glu Arg Thr Asp Asn Asp Ile Lys Asn Tyr Trp Asn Thr His Leu
            100                 105                 110

Lys Lys Lys Leu Lys Lys Met Gln Ala Ala Gly Gly Glu Asp Ser
        115                 120                 125

Gly Ala Ala Ser Glu Gly Gly Gly Arg Gly Asp Gly Asp Gly Gly
    130                 135                 140

Gly Lys Ser Val Lys Ala Ala Pro Lys Gly Gln Trp Glu Arg Arg
145                 150                 155                 160

Leu Gln Thr Asp Ile His Thr Ala Arg Gln Ala Leu Arg Asp Ala Leu
                165                 170                 175

Ser Leu Asp His Pro Asp Pro Ser Pro Ala Thr Ala Ala Ala Ala
            180                 185                 190

Thr Pro Ala Gly Ser Ser Ala Ala Tyr Ala Ser Ala Asp Asn Ile
        195                 200                 205

Ala Arg Leu Leu Gln Gly Trp Met Arg Pro Gly Gly Gly Gly Gly
    210                 215                 220

Asn Gly Lys Gly Pro Glu Ala Ser Gly Ser Thr Ser Thr Ala Thr
225                 230                 235                 240

Thr Gln Gln Gln Pro Gln Cys Ser Gly Glu Ala Ala Ser Ala Ser
                245                 250                 255

Ala Ser Ala Ser Gln Ser Gly Ala Ala Ala Ala Thr Ala Gln Thr
            260                 265                 270

Pro Glu Cys Ser Thr Glu Thr Ser Lys Met Ala Thr Gly Gly Gly Ala
        275                 280                 285

Gly Gly Pro Ala Pro Ala Phe Ser Met Leu Glu Ser Trp Leu Leu Asp
    290                 295                 300

Asp Gly Gly Met Gly Leu Met Asp Val Val Pro Leu Gly Asp Pro Ser
305                 310                 315                 320

Glu Phe Phe

<210> SEQ ID NO 27
<211> LENGTH: 557
<212> TYPE: DNA
<213> ORGANISM: Glycine max
<220> FEATURE:
<221> NAME/KEY: unsure
<222> LOCATION: (136)
<223> OTHER INFORMATION: n is a, c, g or t
<220> FEATURE:
```

```
<221> NAME/KEY: unsure
<222> LOCATION: (229)
<223> OTHER INFORMATION: n is a, c, g or t
<220> FEATURE:
<221> NAME/KEY: unsure
<222> LOCATION: (271)
<223> OTHER INFORMATION: n is a, c, g or t
<220> FEATURE:
<221> NAME/KEY: unsure
<222> LOCATION: (373)
<223> OTHER INFORMATION: n is a, c, g or t
<220> FEATURE:
<221> NAME/KEY: unsure
<222> LOCATION: (382)
<223> OTHER INFORMATION: n is a, c, g or t
<220> FEATURE:
<221> NAME/KEY: unsure
<222> LOCATION: (386)
<223> OTHER INFORMATION: n is a, c, g or t
<220> FEATURE:
<221> NAME/KEY: unsure
<222> LOCATION: (424)
<223> OTHER INFORMATION: n is a, c, g or t
<220> FEATURE:
<221> NAME/KEY: unsure
<222> LOCATION: (475)
<223> OTHER INFORMATION: n is a, c, g or t
<220> FEATURE:
<221> NAME/KEY: unsure
<222> LOCATION: (493)..(494)
<223> OTHER INFORMATION: n is a, c, g or t
<220> FEATURE:
<221> NAME/KEY: unsure
<222> LOCATION: (511)
<223> OTHER INFORMATION: n is a, c, g or t
<220> FEATURE:
<221> NAME/KEY: unsure
<222> LOCATION: (520)
<223> OTHER INFORMATION: n is a, c, g or t
<220> FEATURE:
<221> NAME/KEY: unsure
<222> LOCATION: (522)
<223> OTHER INFORMATION: n is a, c, g or t
<220> FEATURE:
<221> NAME/KEY: unsure
<222> LOCATION: (531)
<223> OTHER INFORMATION: n is a, c, g or t
<220> FEATURE:
<221> NAME/KEY: unsure
<222> LOCATION: (536)
<223> OTHER INFORMATION: n is a, c, g or t
<220> FEATURE:
<221> NAME/KEY: unsure
<222> LOCATION: (552)..(553)
<223> OTHER INFORMATION: n is a, c, g or t

<400> SEQUENCE: 27
tctctctccc ctcttcccca cccaaccttc tctctatcac acacacaaaa caatggataa      60
aaaacaactg tgcaacacgt ctcaagatcc tgaagtgaga aaaggacctt ggacgatgga     120
agaagacttg atcttngatc aactatattg caaatcatgg ggaaggtgtt tggaattctt     180
tggccaaaag ctgctggtct caaacgtacc ggaaagattg ccggctaang tggctaaact     240
acctccgtcc tgatgttaga agagggaata ntacacccga aggaacaact tgatcatgg      300 agcttcacgc aaagtgggga acaggtggt ccaaaattgc caagcatcta cctggtagga     360
cagtaatgag atnaagaact antggnggac aaggatcaga agcacatcaa gcaactgaga     420
attnagcaac aatcacataa ctctgagata atgttacaag ctagatacca agttntacaa     480
ggtgaaccat ggnnactatc ccaaccttt naaggaagtn angcatttct naatcnttcc     540
ccaaataacc gnntatc                                                    557
```

<210> SEQ ID NO 28
<211> LENGTH: 94
<212> TYPE: PRT
<213> ORGANISM: Glycine max
<220> FEATURE:
<221> NAME/KEY: UNSURE
<222> LOCATION: (19)..(20)
<223> OTHER INFORMATION: Xaa can be any naturally occurring amino acid
<220> FEATURE:
<221> NAME/KEY: UNSURE
<222> LOCATION: (51)
<223> OTHER INFORMATION: Xaa can be any naturally occurring amino acid
<220> FEATURE:
<221> NAME/KEY: UNSURE
<222> LOCATION: (65)
<223> OTHER INFORMATION: Xaa can be any naturally occurring amino acid

<400> SEQUENCE: 28

Ser Gln Asp Pro Glu Val Arg Lys Gly Pro Trp Thr Met Glu Glu Asp
 1               5                  10                  15

Leu Ile Xaa Xaa Ile Asn Tyr Ile Ala Asn His Gly Glu Gly Val Trp
             20                  25                  30

Asn Ser Leu Ala Lys Ser Cys Trp Ser Gln Thr Tyr Arg Lys Asp Cys
         35                  40                  45

Arg Leu Xaa Trp Leu Asn Tyr Leu Arg Pro Asp Val Arg Arg Gly Asn
     50                  55                  60

Xaa Thr Pro Glu Gly Thr Thr Leu Ile Met Glu Leu His Ala Lys Trp
 65                  70                  75                  80

Asn Arg Trp Ser Lys Ile Ala Lys His Leu Pro Gly Arg Thr
             85                  90

<210> SEQ ID NO 29
<211> LENGTH: 988
<212> TYPE: DNA
<213> ORGANISM: Glycine max

<400> SEQUENCE: 29
cgcacgagtc tctctcccct cttccccacc caaccttctc tctatcacac acacaaaaca      60
atggataaaa acaactgtgt caacacgtct caagatcctg aagtgagaaa aggaccttgg     120
acgatggaag aagacttgat cttgatcaac tatattgcaa atcatgggga aggtgtttgg     180
aattctttgg ccaaagctgc tggtctcaaa cgtaccggaa agagttgccg gctaaggtgg     240
ctaaactacc tccgtcctga tgttagaaga gggaatatta cacccgagga caacttttg      300 atcatggagc ttcacgcaaa gtggggaaac aggtggtcca aaattgccaa gcatctacct     360
ggtaggacag ataatgagat caagaactat tggaggacca ggatccagaa gcacatcaag     420
caagctgaga ctttcagca acaaatcagc aataactctg agataaatga tcaccaagct      480
agcactagcc atgtttctac catggctgaa cccatggaga cctattctcc acccttttat     540
caaggaatgt tagagccatt ttcttcaatt cagttcccca caattaatcc tgatcaatcc     600
agttgttgta ccaatgacaa caacaacagc attaactatt ggagcatgga ggatatctgg     660
tcaatgcagt tactgaacgg ggattaaata ttgatatatc aagataaacc taaattcttg     720
tataagttcc ataaaacact ggaatgtctc tggcttaaaa catattatta ttaggtttgt     780
ttatataagt agttggatat gtttggtttt gcgtaccatt attagcatat atatatatat     840
ttcaaatgag atgctatgtg cattgtaaaa gatatggtta agaaccacat agtttcaaaa     900
ctcttaaata taattccagt cacttattat aggaagtcta ttattaatta tctccaagat     960
gtttgcttaa aaaaaaaaaa aaaaaaaa                                        988

```
<210> SEQ ID NO 30
<211> LENGTH: 208
<212> TYPE: PRT
<213> ORGANISM: Glycine max

<400> SEQUENCE: 30

Met Asp Lys Lys Gln Leu Cys Asn Thr Ser Gln Asp Pro Glu Val Arg
 1               5                  10                  15

Lys Gly Pro Trp Thr Met Glu Glu Asp Leu Ile Leu Ile Asn Tyr Ile
            20                  25                  30

Ala Asn His Gly Glu Gly Val Trp Asn Ser Leu Ala Lys Ala Ala Gly
        35                  40                  45

Leu Lys Arg Thr Gly Lys Ser Cys Arg Leu Arg Trp Leu Asn Tyr Leu
    50                  55                  60

Arg Pro Asp Val Arg Arg Gly Asn Ile Thr Pro Glu Glu Gln Leu Leu
65                  70                  75                  80

Ile Met Glu Leu His Ala Lys Trp Gly Asn Arg Trp Ser Lys Ile Ala
                85                  90                  95

Lys His Leu Pro Gly Arg Thr Asp Asn Glu Ile Lys Asn Tyr Trp Arg
            100                 105                 110

Thr Arg Ile Gln Lys His Ile Lys Gln Ala Glu Asn Phe Gln Gln Gln
        115                 120                 125

Ile Ser Asn Asn Ser Glu Ile Asn Asp His Gln Ala Ser Thr Ser His
    130                 135                 140

Val Ser Thr Met Ala Glu Pro Met Glu Thr Tyr Ser Pro Pro Phe Tyr
145                 150                 155                 160

Gln Gly Met Leu Glu Pro Phe Ser Ser Ile Gln Phe Pro Thr Ile Asn
                165                 170                 175

Pro Asp Gln Ser Ser Cys Cys Thr Asn Asp Asn Asn Ser Ile Asn
            180                 185                 190

Tyr Trp Ser Met Glu Asp Ile Trp Ser Met Gln Leu Leu Asn Gly Asp
            195                 200                 205

<210> SEQ ID NO 31
<211> LENGTH: 530
<212> TYPE: DNA
<213> ORGANISM: Glycine max
<220> FEATURE:
<221> NAME/KEY: unsure
<222> LOCATION: (301)
<223> OTHER INFORMATION: n is a, c, g or t
<220> FEATURE:
<221> NAME/KEY: unsure
<222> LOCATION: (356)
<223> OTHER INFORMATION: n is a, c, g or t
<220> FEATURE:
<221> NAME/KEY: unsure
<222> LOCATION: (388)
<223> OTHER INFORMATION: n is a, c, g or t
<220> FEATURE:
<221> NAME/KEY: unsure
<222> LOCATION: (393)
<223> OTHER INFORMATION: n is a, c, g or t
<220> FEATURE:
<221> NAME/KEY: unsure
<222> LOCATION: (470)
<223> OTHER INFORMATION: n is a, c, g or t
<220> FEATURE:
<221> NAME/KEY: unsure
<222> LOCATION: (485)
<223> OTHER INFORMATION: n is a, c, g or t
<220> FEATURE:
<221> NAME/KEY: unsure
<222> LOCATION: (495)
```

```
<223> OTHER INFORMATION: n is a, c, g or t
<220> FEATURE:
<221> NAME/KEY: unsure
<222> LOCATION: (513)
<223> OTHER INFORMATION: n is a, c, g or t
<220> FEATURE:
<221> NAME/KEY: unsure
<222> LOCATION: (517)
<223> OTHER INFORMATION: n is a, c, g or t
<220> FEATURE:
<221> NAME/KEY: unsure
<222> LOCATION: (522)
<223> OTHER INFORMATION: n is a, c, g or t

<400> SEQUENCE: 31
aaaataatgg acaagaagct tggcaacacg tctcatgatc ctgaagtgag aaaggggcca    60
tggacaatga agaagactt aatcttgatc acctatattg ccaatcacgg ggaaggggtt   120
tggaactctt tggccaaggc tgctggactt aaacgtaccg aaagagttg ccggctccgg   180
tggctaaact acctccgtcc tgatgttaga gagggaata ttacacccga ggaacagctt   240
ttgatcatgg aacttcatgc aaagtgggga acaggtggt ccaaaattgc caagcatcta   300
nccggaagga ctgataatga gattaagaac tactggagga caaggatcaa gaacanctca   360
agcaagcctt caacaacttc aacaacanag tantaattct gagataattt acatcccaag   420
cttgcacaac caattgtcaa caatgggcaa cccaaaaaaa ctaatctcan caatttcaag   480
gaagnttatt cattnaatca attccaaaaa ccncacntct antgtttcaa              530

<210> SEQ ID NO 32
<211> LENGTH: 204
<212> TYPE: PRT
<213> ORGANISM: Glycine max

<400> SEQUENCE: 32

Met Asp Lys Lys Leu Gly Asn Thr Ser His Asp Pro Glu Val Arg Lys
 1               5                  10                  15

Gly Pro Trp Thr Met Glu Glu Asp Leu Ile Leu Ile Thr Tyr Ile Ala
            20                  25                  30

Asn His Gly Glu Gly Val Trp Asn Ser Leu Ala Lys Ala Ala Gly Leu
        35                  40                  45

Lys Arg Thr Gly Lys Ser Cys Arg Leu Arg Trp Leu Asn Tyr Leu Arg
    50                  55                  60

Pro Asp Val Arg Arg Gly Asn Ile Thr Pro Glu Glu Gln Leu Leu Ile
65                  70                  75                  80

Met Glu Leu His Ala Lys Trp Gly Asn Arg Trp Ser Lys Ile Ala Lys
                85                  90                  95

His Leu Pro Gly Arg Thr Asp Asn Glu Ile Lys Asn Tyr Trp Arg Thr
            100                 105                 110

Arg Ile Gln Lys His Leu Lys Gln Ala Ser Ser Phe Gln Gln Gln
        115                 120                 125

Ser Ser Asn Ser Glu Ile Ile Tyr His Pro Gln Ala Cys Thr Ser Gln
    130                 135                 140

Val Ser Thr Met Ala Gln Pro Ile Glu Thr Tyr Ser Pro Pro Ser Tyr
145                 150                 155                 160

Gln Gly Met Leu Asp Pro Phe Ser Ile Gln Phe Pro Thr Asn Pro His
                165                 170                 175

His Ser Ser Cys Cys Thr Asn Asp Asp Asn Asn Tyr Trp Ser
            180                 185                 190

Met Glu Asp Ile Trp Ser Met Gln Leu Ala Asn Tyr
```

<210> SEQ ID NO 33
<211> LENGTH: 910
<212> TYPE: DNA
<213> ORGANISM: Glycine max
<220> FEATURE:
<221> NAME/KEY: unsure
<222> LOCATION: (798)
<223> OTHER INFORMATION: n is a, c, g or t
<220> FEATURE:
<221> NAME/KEY: unsure
<222> LOCATION: (807)
<223> OTHER INFORMATION: n is a, c, g or t
<220> FEATURE:
<221> NAME/KEY: unsure
<222> LOCATION: (814)
<223> OTHER INFORMATION: n is a, c, g or t

<400> SEQUENCE: 33

```
tctctctctc tctctctcta gcgtgcacac aaaataatgg acaaaaaacc atgcgactca      60
tctcatgatc cagaagtgag aaagggacca tggatcatgg aagaagactt gatcttgata     120
aactatattg caaatcacgg tgaaggtgtt tggaattctt tagccaaagc ttctggtctt     180
aaacgaacgg gaaagagttg tcgactccgt tggctaaact accttcgtcc tgatgttaga     240
agaggaaaca ttcacccga agaacagctt ttgatcatag aacttcatgc aaagtggggc     300
aataggtggt ccaaaattgc aaagcatctt ccaggaagaa ctgacaatga gattaagaac     360
ttctggagaa ctaggatcca gaagcacatt aagcaagctg agacttcaca acaacatggt     420
aattcatcag agaatagtaa taatgatcat caagcaagca atagcactag caaggtgtcc     480
accatggcac atccaaatga gactttctct tcaccctcat accaagcaac ttttgagcca     540
tttcaacctc aattcctaca atcaatgatc aatcaagttg ttgtaccagc aacaacaact     600
attggagcat cgaggatatc tggtcgtcta tgcaattact caatggagat waattaaatc     660
tagctatatg catgcttata taaatcatat atgtgatgat atataaacct aagctcttat     720
tgagtgtggt caggcttaat aacatcatta ggtctggtat atatgagtag gttaagattg     780
gtgtgcatgc ctaaatgnag tattgcntta ttgnagtaag aataactagt tatggatgcc     840
tttaaaaaaa agttagttat gaattgaaat atatagtaac ttatatacta aaaaaaaaa     900
aaaaaaaaaa                                                            910
```

<210> SEQ ID NO 34
<211> LENGTH: 206
<212> TYPE: PRT
<213> ORGANISM: Glycine max

<400> SEQUENCE: 34

```
Met Asp Lys Lys Pro Cys Asp Ser Ser His Asp Pro Glu Val Arg Lys
 1               5                  10                  15

Gly Pro Trp Ile Met Glu Glu Asp Leu Ile Leu Ile Asn Tyr Ile Ala
                20                  25                  30

Asn His Gly Glu Gly Val Trp Asn Ser Leu Ala Lys Ala Ser Gly Leu
            35                  40                  45

Lys Arg Thr Gly Lys Ser Cys Arg Leu Arg Trp Leu Asn Tyr Leu Arg
        50                  55                  60

Pro Asp Val Arg Arg Gly Asn Ile Thr Pro Glu Glu Gln Leu Leu Ile
65                  70                  75                  80

Ile Glu Leu His Ala Lys Trp Gly Asn Arg Trp Ser Lys Ile Ala Lys
                85                  90                  95
```

His Leu Pro Gly Arg Thr Asp Asn Glu Ile Lys Asn Phe Trp Arg Thr
              100                 105                 110

Arg Ile Gln Lys His Ile Lys Gln Ala Glu Thr Ser Gln Gln His Gly
          115                 120                 125

Asn Ser Ser Glu Asn Ser Asn Asp His Gln Ala Ser Asn Ser Thr
    130                 135                 140

Ser Lys Val Ser Thr Met Ala His Pro Asn Glu Thr Phe Ser Ser Pro
145                 150                 155                 160

Ser Tyr Gln Ala Thr Phe Glu Pro Phe Gln Pro Gln Phe Leu Gln Ser
              165                 170                 175

Met Ile Asn Gln Val Val Pro Ala Thr Thr Thr Ile Gly Ala Ser
          180                 185                 190

Arg Ile Ser Gly Arg Leu Cys Asn Tyr Ser Met Glu Ile Asn
      195                 200                 205

<210> SEQ ID NO 35
<211> LENGTH: 863
<212> TYPE: DNA
<213> ORGANISM: Glycine max

<400> SEQUENCE: 35
gcacgagctc tatcacacac acaagtcaat ggataaaaaa caacagtgta agacgtctca      60
agatcctgaa gtgagaaaag ggccttggac aatggaagaa gacttgatct tgatgaacta     120
tattgcaaat catggggaag gtgtttggaa ctctttggcc aaagctgctg gtctcaaacg     180
taacggaaag agttgccggc taaggtggct aaattacctc cgtcctgatg ttagaagagg     240
gaatattaca cccgaggaac aactttgat tatggagctc cacgcaaagt ggggaaacag     300
gtggtccaaa attgccaagc atctacctgg aaggactgat aatgagatca gaactattg     360
gaggacaagg atccagaagc acatcaagca agctgagaac tttcagcaac agagtagtaa     420
taattctgag ataaatgatc accaagctag cactagccat gtttccacca tggctgagcc     480
catggagatg tattctccac cctgttatca aggaatgtta gagccatttt caactcagtt     540
ccctacaatt aatcctgatc aatccagttg ttgtaccaat gacaacaaca acattaacta     600
ttggagcatg gaggatagct ggtcaatgca attactgaac ggtgattaaa tattatcaag     660
ataaaaccta agttytgaag ttccataagg ctggaatgtc tytggattaa acatatta      720
tgggtttgtt tatataagta gttggatgtt tggttttgcg taccattatt agctatgtgc     780
tgtaatatat acgagatytt atattaaact atatctgcat gctttatata taaaaaaaaa     840
aaaaaaaaaa aaaaaaaaa aaa                                              863

<210> SEQ ID NO 36
<211> LENGTH: 206
<212> TYPE: PRT
<213> ORGANISM: Glycine max

<400> SEQUENCE: 36

Met Asp Lys Lys Gln Gln Cys Lys Thr Ser Gln Asp Pro Glu Val Arg
1               5                  10                  15

Lys Gly Pro Trp Thr Met Glu Glu Asp Leu Ile Leu Met Asn Tyr Ile
              20                  25                  30

Ala Asn His Gly Glu Gly Val Trp Asn Ser Leu Ala Lys Ala Ala Gly
          35                  40                  45

Leu Lys Arg Asn Gly Lys Ser Cys Arg Leu Arg Trp Leu Asn Tyr Leu
    50                  55                  60

```
Arg Pro Asp Val Arg Arg Gly Asn Ile Thr Pro Glu Glu Gln Leu Leu
 65                  70                  75                  80

Ile Met Glu Leu His Ala Lys Trp Gly Asn Arg Trp Ser Lys Ile Ala
                 85                  90                  95

Lys His Leu Pro Gly Arg Thr Asp Asn Glu Ile Lys Asn Tyr Trp Arg
            100                 105                 110

Thr Arg Ile Gln Lys His Ile Lys Gln Ala Glu Asn Phe Gln Gln Gln
        115                 120                 125

Ser Ser Asn Asn Ser Glu Ile Asn Asp His Gln Ala Ser Thr Ser His
130                 135                 140

Val Ser Thr Met Ala Glu Pro Met Glu Met Tyr Ser Pro Pro Cys Tyr
145                 150                 155                 160

Gln Gly Met Leu Glu Pro Phe Ser Thr Gln Phe Pro Thr Ile Asn Pro
                165                 170                 175

Asp Gln Ser Ser Cys Cys Thr Asn Asp Asn Asn Asn Ile Asn Tyr Trp
            180                 185                 190

Ser Met Glu Asp Ser Trp Ser Met Gln Leu Leu Asn Gly Asp
        195                 200                 205

<210> SEQ ID NO 37
<211> LENGTH: 805
<212> TYPE: DNA
<213> ORGANISM: Glycine max

<400> SEQUENCE: 37
aaaaaaccat gcaactcatc atctcatgat cctgaagtga aaagggacc atggaccatg      60 gaagaagact tgatcttgat aaactatatt gcaaatcacg gtgaaggtgt ttggaactcc     120
ttagccaaag cttctggtct caacgaacg ggaaagagtt gtcgactccg ttggctaaac      180
taccttcgtc ctgatgttag aagaggaaac attacacccg aggaacagct tttgatcata     240
gaacttcatg caaagtgggg caataggtgg tccaaaattg caaagcatct tccaggaaga     300
actgacaatg agattaagaa cttctggaga caaggatcc aaaagcacat taagcaagct      360
gagacttcac aacaacatgg taattcagag aataatgatc atcaagcaag cactagtact     420
agcaaagtgt ccaccatggc acatccaaat gagactttct ctccacccte ataccaagga    480 acttttgagc cattccaacc tcaattccct acaatcactg atcaatcaag ttgttgtacc    540
accaccaacg acaacaacaa ctattggagc atcgaggata tctggtcgtc tatgcaatta   600
ctcaatggag attaaaccta gctatatgca tgcctatata aatcatatat atgatgatat     660
ataaacctaa gctcttgtag agtgtgttca ggcttaataa catcattagg tctgtttata    720
tgagtagtct aagtttggtg tttgtaatgc atgatgtgag ttaagaatta atttagttat    780
ggttggaaaa aaaaaaaaaa aaaaa                                          805

<210> SEQ ID NO 38
<211> LENGTH: 204
<212> TYPE: PRT
<213> ORGANISM: Glycine max

<400> SEQUENCE: 38

Lys Lys Pro Cys Asn Ser Ser His Asp Pro Glu Val Arg Lys Gly
  1               5                  10                  15

Pro Trp Thr Met Glu Glu Asp Leu Ile Leu Ile Asn Tyr Ile Ala Asn
                 20                  25                  30

His Gly Glu Gly Val Trp Asn Ser Leu Ala Lys Ala Ser Gly Leu Lys
```

```
                  35                  40                  45
Arg Thr Gly Lys Ser Cys Arg Leu Arg Trp Leu Asn Tyr Leu Arg Pro
     50                  55                  60

Asp Val Arg Arg Gly Asn Ile Thr Pro Glu Glu Gln Leu Leu Ile Ile
 65                  70                  75                  80

Glu Leu His Ala Lys Trp Gly Asn Arg Trp Ser Lys Ile Ala Lys His
                 85                  90                  95

Leu Pro Gly Arg Thr Asp Asn Glu Ile Lys Asn Phe Trp Arg Thr Arg
            100                 105                 110

Ile Gln Lys His Ile Lys Gln Ala Glu Thr Ser Gln Gln His Gly Asn
        115                 120                 125

Ser Glu Asn Asn Asp His Gln Ala Ser Thr Ser Thr Ser Lys Val Ser
    130                 135                 140

Thr Met Ala His Pro Asn Glu Thr Phe Ser Pro Pro Ser Tyr Gln Gly
145                 150                 155                 160

Thr Phe Glu Pro Phe Gln Pro Gln Phe Pro Thr Ile Thr Asp Gln Ser
                165                 170                 175

Ser Cys Cys Thr Thr Thr Asn Asp Asn Asn Asn Tyr Trp Ser Ile Glu
            180                 185                 190

Asp Ile Trp Ser Ser Met Gln Leu Leu Asn Gly Asp
        195                 200
```

<210> SEQ ID NO 39
<211> LENGTH: 751
<212> TYPE: DNA
<213> ORGANISM: Glycine max

<400> SEQUENCE: 39

```
tggatgttaa gaaaggtggg tctgtagtac aagcacaagt gaagttgcag aagcataacg      60
aaaaggagat gggcatgaga aaaggtccat gggcggttga ggaggacacc attctggtca     120
attacatcgc cacacacggt gaaggccact ggaattccgt ggcacgatgt gcaggtctaa     180
ggaggagtgg gaaagagttgc agattaaggt ggctaaacta cttgcgccca gacgtgcggc     240
gtggaaatat cacactccaa gaacaaatat taattctcga ccttcactct cgctgggca     300
acaggtggtc aaagattgct caacagctgc aggaagaac agacaacgaa ataaagaact     360
attggaggac agagtgata aaacaagcga agcagctaaa gtgcgatgtg aatagcaaac     420
agttcagaga cacgttgcgt tacgtttgga tgccgcgctt gctggagcgg cttcagccca     480
catcacaagc actggagcca aaccaaagtg gacttgtgtt acacgcttca tcatcactgc     540
ttccttcgaa ttccgaccat agtattgaaa ggggtcgga tctgtggcca ggtttcaata     600
accaaatgtt gttggaacag gggagtggcg gtgacttgtt ggaaagtttg tgggatgacg     660
acaatatgtg cttttgcaa cagctttctt atgacctcca aatgaaataa aatacaattc     720
ccttccgtca cgcaaaaaaa aaaaaaaaaa a                                    751
```

<210> SEQ ID NO 40
<211> LENGTH: 235
<212> TYPE: PRT
<213> ORGANISM: Glycine max

<400> SEQUENCE: 40

```
Asp Val Lys Lys Gly Gly Ser Val Val Gln Ala Gln Val Lys Leu Gln
 1               5                  10                  15

Lys His Asn Glu Lys Glu Met Gly Met Arg Lys Gly Pro Trp Ala Val
             20                  25                  30
```

```
Glu Glu Asp Thr Ile Leu Val Asn Tyr Ile Ala Thr His Gly Glu Gly
         35                  40                  45

His Trp Asn Ser Val Ala Arg Cys Ala Gly Leu Arg Arg Ser Gly Lys
 50                  55                  60

Ser Cys Arg Leu Arg Trp Leu Asn Tyr Leu Arg Pro Asp Val Arg Arg
 65                  70                  75                  80

Gly Asn Ile Thr Leu Gln Glu Gln Ile Leu Ile Leu Asp Leu His Ser
                 85                  90                  95

Arg Trp Gly Asn Arg Trp Ser Lys Ile Ala Gln Gln Leu Pro Gly Arg
            100                 105                 110

Thr Asp Asn Glu Ile Lys Asn Tyr Trp Arg Thr Arg Val Ile Lys Gln
        115                 120                 125

Ala Lys Gln Leu Lys Cys Asp Val Asn Ser Lys Gln Phe Arg Asp Thr
130                 135                 140

Leu Arg Tyr Val Trp Met Pro Arg Leu Leu Glu Arg Leu Gln Pro Thr
145                 150                 155                 160

Ser Gln Ala Leu Glu Pro Asn Gln Ser Gly Leu Val Leu His Ala Ser
                165                 170                 175

Ser Ser Leu Leu Pro Ser Asn Ser Asp His Ser Ile Glu Arg Gly Ser
            180                 185                 190

Asp Leu Trp Pro Gly Phe Asn Asn Gln Met Leu Leu Glu Gln Gly Ser
        195                 200                 205

Gly Gly Asp Leu Leu Glu Ser Leu Trp Asp Asp Asn Met Cys Phe
210                 215                 220

Leu Gln Gln Leu Ser Tyr Asp Leu Gln Met Lys
225                 230                 235

<210> SEQ ID NO 41
<211> LENGTH: 500
<212> TYPE: DNA
<213> ORGANISM: Glycine max

<400> SEQUENCE: 41
catttctaat tgttctgatc catatatatc atactttctt tgtaataact taagaaccc      60 cacaaaaaca ccaaccatgt ccacaattgc aaagagagat tgagttcta atgaagaaga    120 gagtgagctg agaagaggtc cttggactct tgaagaagac agcttactca tacactatat   180
tgctcgtcat ggtgaaggcc gttgaatat gttagccaaa agtgcaggat tgaagaggac    240
tggaaaaagt tgcagactta gatggctgaa ttatttgaaa ccagacatta agagagggaa   300
cctcactcca caggagcaac tcttgatcct tgaactccat ccaagtggg gtaacaggtg    360 gtcaaaaatt gctcagcatc tgccaggaag aacagacaat gagatcaaga actattggag   420
aacaaggata cagaaacagg gcacgccaac ttaacattga atctggtagc aagagattca    480
ttgatgctgt cagtgttttt                                                 500

<210> SEQ ID NO 42
<211> LENGTH: 229
<212> TYPE: PRT
<213> ORGANISM: Glycine max
<220> FEATURE:
<221> NAME/KEY: UNSURE
<222> LOCATION: (138)
<223> OTHER INFORMATION: Xaa can be any naturally occurring amino acid

<400> SEQUENCE: 42

Met Ser Thr Ile Ala Lys Arg Asp Leu Ser Ser Asn Glu Glu Glu Ser
```

```
                1               5                  10                 15
Glu Leu Arg Arg Gly Pro Trp Thr Leu Glu Glu Asp Ser Leu Leu Ile
                    20                 25                 30

His Tyr Ile Ala Arg His Gly Glu Gly Arg Trp Asn Met Leu Ala Lys
            35                 40                     45

Ser Ala Gly Leu Lys Arg Thr Gly Lys Ser Cys Arg Leu Arg Trp Leu
        50                 55                 60

Asn Tyr Leu Lys Pro Asp Ile Lys Arg Gly Asn Leu Thr Pro Gln Glu
65                      70                 75                 80

Gln Leu Leu Ile Leu Glu Leu His Ser Lys Trp Gly Asn Arg Trp Ser
                    85                 90                 95

Lys Ile Ala Gln His Leu Pro Gly Arg Thr Asp Asn Glu Ile Lys Asn
                100                105                110

Tyr Trp Arg Thr Arg Ile Gln Lys Gln Ala Arg Gln Leu Asn Ile Glu
            115                120                125

Ser Gly Ser Lys Arg Phe Ile Asp Ala Xaa Lys Cys Phe Trp Met Pro
        130                135                140

Arg Leu Leu Gln Lys Met Glu Gln Ser Asn Ser Pro Ser Pro His His
145                 150                155                160

Ser Ser Met Thr Asn Met Met Asn Leu Gly Asn Ser Gly Glu Ala Ser
                165                170                175

Met Ser Ser Met Ser Ser Ser Phe Asn Ile Asn Pro Ser Met Ser Ser
            180                185                190

Ser Ser Ser Pro Pro Lys Gly Asn Leu Leu Trp Met Met Pro Asn His
        195                200                205

Phe Lys Tyr Tyr Val Gln Pro His Gln Ser Ile Pro Arg Phe Leu Pro
    210                215                220

Ile Phe Thr Ala Thr
225

<210> SEQ ID NO 43
<211> LENGTH: 1348
<212> TYPE: DNA
<213> ORGANISM: Glycine max

<400> SEQUENCE: 43
tacctctcca accaagacca atttgaaaac ctcttcaatc caacaaacaa acgttctccc      60
ttttgttctg agagaatcaa tggatggaaa aggagcaaga agtagcaaca ccctttttaag   120 tagtgaggac gagatggacc ttcgaagagg cccttggacc gtcgatgaag acctcactct     180
tatcaattac gttgccactc atggcgaagg tcgctggaat accctcgccc tctctgctgg    240
gctgaaacga acggggaaga gttgcagatt gaggtggctg aattatctgc gtcctgatgt    300
tcgacgtgga acatcacgc ttgaagaaca acttttgatt ctggagctcc attctcgctg     360
gggaaaccga tggtcgaaaa ttgctcaata tttgcctggt agaaccgaca atgagataaa    420
gaactattgg agaacccgtg tccaaaagca tgccaagcaa ctcaaatgcg acgtgaatag    480
caagcaattc aaggacacca tgcgttacat ttggatgcca aggctcgtgg aacgcattca    540
agccaccgct gccgcctccg caccacaacc cgttaccgta ccaccgcgac caacaatgca    600
tacacctacg gaagcaacct taataacaac aaattcgagg ttcacgatca aagggcaaa    660 atggggttaa ccgatccttc agttatgaac aatgacttaa tgggttcaca tgtcacgcaa    720
agttacaccc ctgagaatag tagcaccggt gcgtcatcat cagactcgtt tgggactcaa    780
gtctcagcaa tttctgattt gactgaatat tacactgtca ctggtagtgg taacaataac    840
```

-continued

```
aatactaatt ctgcggatta ttatcaaccc tctcaaatta gttactcgga tagttgcatc      900
acaagcccat ctgggttgtt ccctcaaggg ctagattttc aatccatgga tccaaacacc      960
ccgtggaaca tgcaaagtgg ggactcctct gacagttttt ggaacgttga aagcatgttg     1020
ttcttagagc agcaactcat gaatgacaac atgtgaaaac attgggaata ggaaaataag     1080
acttagatac ggttcttctt agtattgtgt tttaattaaa gttaaagtta acacaagtta     1140
ttgaagtgaa actttaattt taattgaata ataatactga aaacaagagt tgtatttaag     1200
ttttattctt ttatgaatta tgaattagat tgacagaagg ggttgtttgt gaaatataca     1260
ggtgaaagta tagaaagtag caacattaat aaaaaaaaaa aaaaaaaaaa aaaaaaaaaa     1320
aaaaaaaaaa aaaaaaaaaa aaaaaaaa                                        1348
```

<210> SEQ ID NO 44
<211> LENGTH: 196
<212> TYPE: PRT
<213> ORGANISM: Glycine max

<400> SEQUENCE: 44

```
Met Asp Gly Lys Gly Ala Arg Ser Ser Asn Thr Leu Leu Ser Ser Glu
  1               5                  10                  15

Asp Glu Met Asp Leu Arg Arg Gly Pro Trp Thr Val Asp Glu Asp Leu
                 20                  25                  30

Thr Leu Ile Asn Tyr Val Ala Thr His Gly Glu Gly Arg Trp Asn Thr
             35                  40                  45

Leu Ala Leu Ser Ala Gly Leu Lys Arg Thr Gly Lys Ser Cys Arg Leu
         50                  55                  60

Arg Trp Leu Asn Tyr Leu Arg Pro Asp Val Arg Arg Gly Asn Ile Thr
 65                  70                  75                  80

Leu Glu Glu Gln Leu Leu Ile Leu Glu Leu His Ser Arg Trp Gly Asn
                 85                  90                  95

Arg Trp Ser Lys Ile Ala Gln Tyr Leu Pro Gly Arg Thr Asp Asn Glu
                100                 105                 110

Ile Lys Asn Tyr Trp Arg Thr Arg Val Gln Lys His Ala Lys Gln Leu
            115                 120                 125

Lys Cys Asp Val Asn Ser Lys Gln Phe Lys Asp Thr Met Arg Tyr Ile
        130                 135                 140

Trp Met Pro Arg Leu Val Glu Arg Ile Gln Ala Thr Ala Ala Ala Ser
145                 150                 155                 160

Ala Pro Gln Pro Val Thr Val Pro Pro Arg Pro Thr Met His Thr Pro
                165                 170                 175

Thr Glu Ala Thr Leu Ile Thr Thr Asn Ser Arg Phe Thr Ile Thr Arg
            180                 185                 190

Ala Lys Trp Gly
        195
```

<210> SEQ ID NO 45
<211> LENGTH: 1236
<212> TYPE: DNA
<213> ORGANISM: Glycine max
<220> FEATURE:
<221> NAME/KEY: unsure
<222> LOCATION: (519)
<223> OTHER INFORMATION: n is a, c, g or t
<220> FEATURE:
<221> NAME/KEY: unsure
<222> LOCATION: (521)
<223> OTHER INFORMATION: n is a, c, g or t

```
<220> FEATURE:
<221> NAME/KEY: unsure
<222> LOCATION: (530)..(531)
<223> OTHER INFORMATION: n is a, c, g or t
<220> FEATURE:
<221> NAME/KEY: unsure
<222> LOCATION: (534)
<223> OTHER INFORMATION: n is a, c, g or t
<220> FEATURE:
<221> NAME/KEY: unsure
<222> LOCATION: (800)
<223> OTHER INFORMATION: n is a, c, g or t
<220> FEATURE:
<221> NAME/KEY: unsure
<222> LOCATION: (1124)
<223> OTHER INFORMATION: n is a, c, g or t
<220> FEATURE:
<221> NAME/KEY: unsure
<222> LOCATION: (1151)
<223> OTHER INFORMATION: n is a, c, g or t

<400> SEQUENCE: 45
aacaatccaa ctctctttct ccctatccca acaatctcac tcatacctct tcaatctaac       60
aaacttaatt tcttttgttt tgagtttctt agagaatgga tgaaaaagga gcaagaagta      120
gcaacaccct tttaagttgt gaggacgaga tggaccttcg aagaggccct tggaccgtcg      180
atgaagacct cactcttatc aattacattg ccactcatgg cgaaggtcgc tggaacacgc      240
tcgccctctc tgctgggctg aaacgaacgg ggaagagttg cagattgagg tggctgaatt      300
atctgcgtcc tgatgttcga cgtggaaaca tcacacttga agaacaactt ttgattctgg      360
agcttcattc tcgctgggga aaccgttggt cgaaaattgc tcaatatttg cctggtagaa      420
ccgacaacga gataaagaac tattggagaa cccgtgtcca aaagcatgcc aagcaactca      480
aatgtgacgt gaatagcaag caattcaagg acaccatgng ntacctttgn natnccaagg      540
ctcgtggaac gcattcaagc agcggcgacg gccccgtaa ccaccaccgt aactgcggcc       600
gccaccaaca atgcattcac ctacggraac aaccttatac caccaaattc gaggttctga      660
atcacaaggg cagaatgggg ttaaccgatc cttcagttgc gaacaatgac tttgtgggtt      720
cacatgtcac gcaaaggtac cctactcctg agaatagtag cacgggtgcg tcatcatcag      780
actcgtttgg gactcaagtn tcaacaattt ctgatttgac tgaaaattcc agtgtccctg      840
aaaatactaa ttctgcggat tattatcaac cctctcaaat tagtaattac tcggataatt      900
gcatcacaag cccatctggg ttcttgttcc ctcaaggact agatcttcaa tccatggatc      960
caaacacacc gtggaacatg caaagtgggg actcctctga caattttttgg gacgttgaaa    1020
gcatgttatt cttagagcag caactcatga atgacaacat gtgaaacatt gggaataggga    1080
aaataagact tagatacggt tcttctaata tttttttagtg ktgngtttta attaaagtta    1140
aagttaacac nagttattga agtgaaactt taattttaat taaataataa tcctgaaaaa    1200
aaaaaaaaaa aaaaaaaaaa aaaaaaaaaa aaaaaa                               1236

<210> SEQ ID NO 46
<211> LENGTH: 322
<212> TYPE: PRT
<213> ORGANISM: Glycine max
<220> FEATURE:
<221> NAME/KEY: UNSURE
<222> LOCATION: (142)
<223> OTHER INFORMATION: Xaa can be any naturally occurring amino acid
<220> FEATURE:
<221> NAME/KEY: UNSURE
<222> LOCATION: (145)..(146)..(147)
<223> OTHER INFORMATION: Xaa can be any naturally occurring amino acid
<220> FEATURE:
```

<221> NAME/KEY: UNSURE
<222> LOCATION: (178)
<223> OTHER INFORMATION: Xaa can be any naturally occurring amino acid

<400> SEQUENCE: 46

```
Met Asp Glu Lys Gly Ala Arg Ser Ser Asn Thr Leu Leu Ser Cys Glu
 1               5                  10                  15
Asp Glu Met Asp Leu Arg Arg Gly Pro Trp Thr Val Asp Glu Asp Leu
             20                  25                  30
Thr Leu Ile Asn Tyr Ile Ala Thr His Gly Glu Gly Arg Trp Asn Thr
         35                  40                  45
Leu Ala Leu Ser Ala Gly Leu Lys Arg Thr Gly Lys Ser Cys Arg Leu
     50                  55                  60
Arg Trp Leu Asn Tyr Leu Arg Pro Asp Val Arg Arg Gly Asn Ile Thr
 65                  70                  75                  80
Leu Glu Glu Gln Leu Leu Ile Leu Glu Leu His Ser Arg Trp Gly Asn
                 85                  90                  95
Arg Trp Ser Lys Ile Ala Gln Tyr Leu Pro Gly Arg Thr Asp Asn Glu
            100                 105                 110
Ile Lys Asn Tyr Trp Arg Thr Arg Val Gln Lys His Ala Lys Gln Leu
        115                 120                 125
Lys Cys Asp Val Asn Ser Lys Gln Phe Lys Asp Thr Met Xaa Tyr Leu
    130                 135                 140
Xaa Xaa Xaa Lys Ala Arg Gly Thr His Ser Ser Ser Gly Asp Gly Pro
145                 150                 155                 160
Arg Asn His His Arg Asn Cys Gly Arg His Gln Gln Cys Ile His Leu
                165                 170                 175
Arg Xaa Gln Pro Tyr Thr Thr Lys Phe Glu Val Leu Asn His Lys Gly
            180                 185                 190
Arg Met Gly Leu Thr Asp Pro Ser Val Ala Asn Asn Asp Phe Val Gly
        195                 200                 205
Ser His Val Thr Gln Arg Tyr Pro Thr Pro Glu Asn Ser Ser Thr Gly
    210                 215                 220
Ala Ser Ser Ser Asp Ser Phe Gly Thr Gln Val Ser Thr Ile Ser Asp
225                 230                 235                 240
Leu Thr Glu Asn Ser Ser Val Pro Glu Asn Thr Asn Ser Ala Asp Tyr
                245                 250                 255
Tyr Gln Pro Ser Gln Ile Ser Asn Tyr Ser Asp Asn Cys Ile Thr Ser
            260                 265                 270
Pro Ser Gly Phe Leu Phe Pro Gln Gly Leu Asp Leu Gln Ser Met Asp
        275                 280                 285
Pro Asn Thr Pro Trp Asn Met Gln Ser Gly Asp Ser Ser Asp Asn Phe
    290                 295                 300
Trp Asp Val Glu Ser Met Leu Phe Leu Glu Gln Gln Leu Met Asn Asp
305                 310                 315                 320
Asn Met
```

<210> SEQ ID NO 47
<211> LENGTH: 1181
<212> TYPE: DNA
<213> ORGANISM: Glycine max

<400> SEQUENCE: 47
tttcagtgag tgagaatagc catgtctact tcaaagagcg tcagcagttc tagtgaagat      60
gacaatgaac ttagaagagg gccttggact ctggaagagg ataacttgct ctcccaatat     120

```
attttttaatc atggggaagg gcgatggaat tgctggcta  aacgttcagg attaaagaga    180
actgggaaaa gttgcagatt aaggtggcta aattatctaa agccagatgt aaaacgggga    240
aatttaaccc cacaagagca acttataatt cttgaactcc actcaaagtg gggaaacagg    300
tggtcaaaaa ttgcacaaca tttgccaggc agaacagaca atgaaatcaa gaactattgg    360
agaactagga ttcagaaaca agcaagacat ttgaaaattt acactgacag cagagagttt    420
caagaacttg ttaggcgttt ctggatgcct agattgcttc agaaagcaaa agaatcatct    480
tcttcaaaca tgtcaattca aaaccaggca attcctatgc cttttgatta tgtttctcag    540
catttaactg ttgggaccat acctccttgg cagggacctt gtatgaatga agctggtccc    600
acttacatgg accaacatga gcagactcag actcggaaca ccaacaatgg ttcatgcatc    660
tccttgtctg agtcagcaaa tattccaaaa gtgcctcagc attttggaca caccaccatc    720
acccaatttc atgccttgaa taccaatgac tttggcacct tcacatatga aggttataat    780
gtaaacaaca atgtctatga gatggacaac ttcaaaacga ctactacatg ggtggctgag    840
gatgcgcaat acccaattgg tgattgtcaa atggtaggaa gcaattgggt aaacaacgat    900
tttgcatgta acatgtggaa catggatgaa ctgtggcagt ttagcaagtt acaaaaataa    960
gattttaggg ttttgttttt tttggaataa ccaaaagtcc aaaactcttt ctttgatgac   1020
gttattattg ttatcatgaa ctgtggatta gctaccgaat taattaatac agatggcgat   1080
tgttttctgt acatctgtct tgtattactc tgttcagata agtactttttg taatttgtat   1140
tgattgagaa aagtcattaa ttagtcacta gtacaaaaaa a                        1181
```

<210> SEQ ID NO 48
<211> LENGTH: 312
<212> TYPE: PRT
<213> ORGANISM: Glycine max

<400> SEQUENCE: 48

```
Met Ser Thr Ser Lys Ser Val Ser Ser Ser Glu Asp Asp Asn Glu
  1               5                  10                  15

Leu Arg Arg Gly Pro Trp Thr Leu Glu Glu Asp Asn Leu Leu Ser Gln
             20                  25                  30

Tyr Ile Phe Asn His Gly Glu Gly Arg Trp Asn Leu Leu Ala Lys Arg
         35                  40                  45

Ser Gly Leu Lys Arg Thr Gly Lys Ser Cys Arg Leu Arg Trp Leu Asn
     50                  55                  60

Tyr Leu Lys Pro Asp Val Lys Arg Gly Asn Leu Thr Pro Gln Glu Gln
 65                  70                  75                  80

Leu Ile Ile Leu Glu Leu His Ser Lys Trp Gly Asn Arg Trp Ser Lys
                 85                  90                  95

Ile Ala Gln His Leu Pro Gly Arg Thr Asp Asn Glu Ile Lys Asn Tyr
            100                 105                 110

Trp Arg Thr Arg Ile Gln Lys Gln Ala Arg His Leu Lys Ile Tyr Thr
        115                 120                 125

Asp Ser Arg Glu Phe Gln Glu Leu Val Arg Arg Phe Trp Met Pro Arg
    130                 135                 140

Leu Leu Gln Lys Ala Lys Glu Ser Ser Ser Asn Met Ser Ile Gln
145                 150                 155                 160

Asn Gln Ala Ile Pro Met Pro Phe Asp Tyr Val Ser Gln His Leu Thr
                165                 170                 175

Val Gly Thr Ile Pro Pro Trp Gln Gly Pro Cys Met Asn Glu Ala Gly
```

-continued

```
                    180                 185                 190
Pro Thr Tyr Met Asp Gln His Glu Gln Thr Gln Thr Arg Asn Thr Asn
                195                 200                 205

Asn Gly Ser Cys Ile Ser Leu Ser Glu Ser Ala Asn Ile Pro Lys Val
            210                 215                 220

Pro Gln His Phe Gly His Thr Thr Ile Thr Gln Phe His Ala Leu Asn
225                 230                 235                 240

Thr Asn Asp Phe Gly Thr Phe Thr Tyr Glu Gly Tyr Asn Val Asn Asn
                245                 250                 255

Asn Val Tyr Glu Met Asp Asn Phe Lys Thr Thr Thr Trp Val Ala
            260                 265                 270

Glu Asp Ala Gln Tyr Pro Ile Gly Asp Cys Gln Met Val Gly Ser Asn
                275                 280                 285

Trp Val Asn Asn Asp Phe Ala Cys Asn Met Trp Asn Met Asp Glu Leu
            290                 295                 300

Trp Gln Phe Ser Lys Leu Gln Lys
305                 310

<210> SEQ ID NO 49
<211> LENGTH: 1186
<212> TYPE: DNA
<213> ORGANISM: Glycine max

<400> SEQUENCE: 49
aattcggcac gaggccatgt ctacttcaaa gagcgtcagc agttctagtg aagatgacaa      60
tgaacttaga agagggcctt ggactcttga agaggataat ttgctctccc aatatatttc    120
tagtcatgga gaagggcgat ggaatttgct agctaaacgt tcaggattaa agcgaactgg    180
gaaaagttgc agattaaggt ggctaaatta tctaaagcca gatgtaaaac ggggaaattt    240
aaccccacaa gagcaactta taatcctcga actccactca aagtggggaa acaggtggtc    300
aaaaattgca caaaatttgc caggcagaac agacaatgaa atcaagaact attggagaac    360
taggattcag aaacaagcaa gacatttgaa aattgacact gacaccagag agtttcagga    420
acttgttagg cgtttctgga tgcctagatg cttcaaaaag cccaagaatc atcttcttca    480
gccatgtcaa ttcaaaacca ggcaactcct atgccttttg atggtgtttc tcagcattca    540
actgttggga ccataccatc acattcacac accccttggc agggaccttg tatgaatgaa    600
gctggtccca cttacatgga ccaacatgag cagaactcag actctgaaca caacaatggt    660
tcatgcatct ccttgtctga gtcagcaaat tttccaaaag tgcctcagca ttttggacgc    720
accaccatca cccaatatca tgccttgaat aacaatgact ttggcacctt cacatatgac    780
ggctacaatg taagcaacaa tgtctatgag atggacaact caaaacgcc tactacaagg    840
gtggctgagg atgcgcaata cccaactggt gattgtcaaa tggtaggaag caattgggta    900
aacagcgatt tgcatgtaa catgtggaac atggatgaat gtgtggcaatt agcaagtta    960
caaaaataag attttagggt ttggtttttt tggagttacc aagactctat ctttggtgat   1020
gttattattg ttatcatgaa ctgttgatta gctactacca aattaattaa tacagatggt   1080
gattgttttc tgtacatctg ttttgcatta ctctgttttg caatttgtat tgattgagaa   1140
aagtcattaa ttagtcacta gttcaaaaca caaaaaaaaa aaaaaa                   1186

<210> SEQ ID NO 50
<211> LENGTH: 192
<212> TYPE: PRT
<213> ORGANISM: Glycine max
```

<400> SEQUENCE: 50

```
Met Ser Thr Ser Lys Ser Val Ser Ser Ser Glu Asp Asp Asn Glu
1               5                   10                  15

Leu Arg Arg Gly Pro Trp Thr Leu Glu Glu Asp Asn Leu Leu Ser Gln
            20                  25                  30

Tyr Ile Ser Ser His Gly Glu Gly Arg Trp Asn Leu Leu Ala Lys Arg
        35                  40                  45

Ser Gly Leu Lys Arg Thr Gly Lys Ser Cys Arg Leu Arg Trp Leu Asn
    50                  55                  60

Tyr Leu Lys Pro Asp Val Lys Arg Gly Asn Leu Thr Pro Gln Glu Gln
65                  70                  75                  80

Leu Ile Ile Leu Glu Leu His Ser Lys Trp Gly Asn Arg Trp Ser Lys
                85                  90                  95

Ile Ala Gln Asn Leu Pro Gly Arg Thr Asp Asn Glu Ile Lys Asn Tyr
            100                 105                 110

Trp Arg Thr Arg Ile Gln Lys Gln Ala Arg His Leu Lys Ile Asp Thr
        115                 120                 125

Asp Thr Arg Glu Phe Gln Glu Leu Val Arg Arg Phe Trp Met Pro Arg
    130                 135                 140

Cys Phe Lys Lys Pro Lys Asn His Leu Leu Gln Pro Cys Gln Phe Lys
145                 150                 155                 160

Thr Arg Gln Leu Leu Cys Leu Leu Met Val Phe Leu Ser Ile Gln Leu
                165                 170                 175

Leu Gly Pro Tyr His His Ile His Thr Pro Leu Gly Arg Asp Leu Val
            180                 185                 190
```

<210> SEQ ID NO 51
<211> LENGTH: 487
<212> TYPE: DNA
<213> ORGANISM: Glycine max
<220> FEATURE:
<221> NAME/KEY: unsure
<222> LOCATION: (358)
<223> OTHER INFORMATION: n is a, c, g or t
<220> FEATURE:
<221> NAME/KEY: unsure
<222> LOCATION: (429)
<223> OTHER INFORMATION: n is a, c, g or t

<400> SEQUENCE: 51

```
gagaaataaa aagagaagaa agaaaacacg atagtatcat catatcacca ccacacacat      60
agatagagag aggaaaacga cctatatttt ttttcctttg agagcttcag gggctaggaa     120
aattagaagg acagccacaa gtataaaggc ggtgaaataa aagagaaaga caagaaggag     180
acatgggaag accaccttgt tgtgacaaag aagggtcaa gaagggcct tggactcctg      240
aagaagacat catattggtg tcttatattc aggaacatgg tcctggaaat tggagggcag     300
ttcctgccaa acagggttg tcaagatgca gcaagagttg cagacttaga tggacganttt    360
acctgaggcc aggaatcaag cgtggtaact tcacaagaac aagaggagaa gatgataatc     420
catcttcang atctttagg aaacagatgg ggtgcaatag cttcatacct tccacaaagg     480
acaaggg                                                              487
```

<210> SEQ ID NO 52
<211> LENGTH: 90
<212> TYPE: PRT
<213> ORGANISM: Glycine max
<220> FEATURE:

<221> NAME/KEY: UNSURE
<222> LOCATION: (59)
<223> OTHER INFORMATION: Xaa can be any naturally occurring amino acid
<220> FEATURE:
<221> NAME/KEY: UNSURE
<222> LOCATION: (72)
<223> OTHER INFORMATION: Xaa can be any naturally occurring amino acid
<220> FEATURE:
<221> NAME/KEY: UNSURE
<222> LOCATION: (83)
<223> OTHER INFORMATION: Xaa can be any naturally occurring amino acid

<400> SEQUENCE: 52

```
Met Gly Arg Pro Pro Cys Cys Asp Lys Glu Gly Val Lys Lys Gly Pro
 1               5                  10                  15

Trp Thr Pro Glu Glu Asp Ile Ile Leu Val Ser Tyr Ile Gln Glu His
                20                  25                  30

Gly Pro Gly Asn Trp Arg Ala Val Pro Ala Lys Thr Gly Leu Ser Arg
            35                  40                  45

Cys Ser Lys Ser Cys Arg Leu Arg Trp Thr Xaa Tyr Leu Arg Pro Gly
 50                  55                  60

Ile Lys Arg Gly Asn Phe Thr Xaa Glu Gln Glu Glu Lys Met Ile Ile
 65                  70                  75                  80

His Leu Xaa Asp Leu Leu Gly Asn Arg Trp
                85                  90
```

<210> SEQ ID NO 53
<211> LENGTH: 1556
<212> TYPE: DNA
<213> ORGANISM: Glycine max

<400> SEQUENCE: 53

```
gcacgaggag aaataaaaag agaagaaaga aaacacgata gtatcatcat atcaccacca      60
cacacataga tagagagagg aaaacgacct atattttttt tcctttgaga gcttcagggg     120
ctaggaaaat tagaaggaca gccacaagta taaaggcggt gaaataaaag agaaagacaa     180
gaaggagaca tgggaagacc accttgttgt gacaaagaag gggtcaagaa agggccttgg     240
actcctgaag aagacatcat attggtgtct tatattcagg aacatggtcc tggaaattgg     300
agggcagttc ctgccaaaac agggttgtca gatgcagca agagttgcag acttagatgg     360
acgaattacc tgaggccagg aatcaagcgt ggtaacttca cagaacaaga ggagaagatg     420
ataatccatc ttcaagatct tttaggaaac agatgggctg caatagcttc ataccttcca     480
caaagaacag acaatgacat aaagaactat tggaataccc atttgagaaa gaagctgaag     540
aagatgcaag caggcggtga aggtggtagc tttggagaag ggttttcagc ctcaaggcaa     600
atccctagag gccagtggga agaaggctc caaactgata tccaaatggc aaagagagcc     660
ctcagtgaag ctctttcacc agagaaaaag ccatcttgtt tatctgcctc aaactcaaac     720
ccttcagata gtagcagctc cttctcttcc acaaaaccaa caacaacaca atctgtgtgc     780
tatgcatcaa gtgctgacaa catagctaga atgctcaagg gttggatgaa gaacccacca     840
aagtcctcaa gaaccaactc gtctatgact cagaactcat tcaacaactt agcaggtgct     900
gatactgctt gtagtagtgg agcaaaggga ccactaagca gtgccgaatt gtctgagaat     960
aattttgaat ccttgtttga ttttgatcag tctttggagt cttcaaactc tgatcaattc    1020
tctcagtcct tgtctcctga ggccactgtt ttgcaagatg aaagcaagcc tgatattaat    1080
attgctgcag aaattatgcc cttctctttg cttgagaaat ggctccttga tgaggcaggt    1140
tgccaagaga aattagttgg ttgttgtggt gatgccaagt ttttctaagt tgggttcatt    1200
```

```
ttgtgacata tgagactgtg ggattttttt attttatttt attttatttc ataagttata    1260
ggtagggcct catcaattaa tctcgcttcg gccttattag agagagaagt tttccagcct    1320
ttggtgctag acgtgtatat gttaattatt attgacatta tgatgattat tatcatactg    1380
tgttagttgc catacactgg caaacttgct tctcttatgt aaagttgatc ttgcgacgag    1440
atcctgcttt atggctttag gcagcgcgac cggtcttctc tctttgtgtc gcttgattag    1500
taaccccccc cggggggggc ccgggtccaa atcccccta atggggtcct ttttag        1556
```

<210> SEQ ID NO 54
<211> LENGTH: 332
<212> TYPE: PRT
<213> ORGANISM: Glycine max

<400> SEQUENCE: 54

```
Met Gly Arg Pro Pro Cys Cys Asp Lys Glu Gly Val Lys Lys Gly Pro
  1               5                  10                  15

Trp Thr Pro Glu Glu Asp Ile Ile Leu Val Ser Tyr Ile Gln Glu His
             20                  25                  30

Gly Pro Gly Asn Trp Arg Ala Val Pro Ala Lys Thr Gly Leu Ser Arg
         35                  40                  45

Cys Ser Lys Ser Cys Arg Leu Arg Trp Thr Asn Tyr Leu Arg Pro Gly
     50                  55                  60

Ile Lys Arg Gly Asn Phe Thr Glu Gln Glu Glu Lys Met Ile Ile His
 65                  70                  75                  80

Leu Gln Asp Leu Leu Gly Asn Arg Trp Ala Ala Ile Ala Ser Tyr Leu
                 85                  90                  95

Pro Gln Arg Thr Asp Asn Asp Ile Lys Asn Tyr Trp Asn Thr His Leu
            100                 105                 110

Arg Lys Lys Leu Lys Lys Met Gln Ala Gly Gly Glu Gly Gly Ser Phe
        115                 120                 125

Gly Glu Gly Phe Ser Ala Ser Arg Gln Ile Pro Arg Gly Gln Trp Glu
    130                 135                 140

Arg Arg Leu Gln Thr Asp Ile Gln Met Ala Lys Arg Ala Leu Ser Glu
145                 150                 155                 160

Ala Leu Ser Pro Glu Lys Lys Pro Ser Cys Leu Ser Ala Ser Asn Ser
                165                 170                 175

Asn Pro Ser Asp Ser Ser Ser Phe Ser Ser Thr Lys Pro Thr Thr
            180                 185                 190

Thr Gln Ser Val Cys Tyr Ala Ser Ala Asp Asn Ile Ala Arg Met
        195                 200                 205

Leu Lys Gly Trp Met Lys Asn Pro Pro Lys Ser Ser Arg Thr Asn Ser
210                 215                 220

Ser Met Thr Gln Asn Ser Phe Asn Asn Leu Ala Gly Ala Asp Thr Ala
225                 230                 235                 240

Cys Ser Ser Gly Ala Lys Gly Pro Leu Ser Ser Ala Glu Leu Ser Glu
                245                 250                 255

Asn Asn Phe Glu Ser Leu Phe Asp Phe Asp Gln Ser Leu Glu Ser Ser
            260                 265                 270

Asn Ser Asp Gln Phe Ser Gln Ser Leu Ser Pro Glu Ala Thr Val Leu
        275                 280                 285

Gln Asp Glu Ser Lys Pro Asp Ile Asn Ile Ala Ala Glu Ile Met Pro
    290                 295                 300

Phe Ser Leu Leu Glu Lys Trp Leu Leu Asp Glu Ala Gly Cys Gln Glu
```

Lys Leu Val Gly Cys Cys Gly Asp Ala Lys Phe Phe
              325                 330

<210> SEQ ID NO 55
<211> LENGTH: 357
<212> TYPE: DNA
<213> ORGANISM: Triticum aestivum
<220> FEATURE:
<221> NAME/KEY: unsure
<222> LOCATION: (259)
<223> OTHER INFORMATION: n is a, c, g or t
<220> FEATURE:
<221> NAME/KEY: unsure
<222> LOCATION: (307)
<223> OTHER INFORMATION: n is a, c, g or t
<220> FEATURE:
<221> NAME/KEY: unsure
<222> LOCATION: (319)
<223> OTHER INFORMATION: n is a, c, g or t

<400> SEQUENCE: 55
gccaaagtat caggtttgag gggtggggga tccaaaaatt aggtagctat attgaagtat    60
tttgcgcaaa gtcgcaacaa caaatgtcac ctttgctaat aactttcttc ttgcttcaac   120
ctctgtaatc tccatgcagg cctcaaccgc acaggaaaga gctgtcgcct ccggtgggtt   180
aactacctcc accctgggcc taaagcgtgg gcgcatgact ccccatgaaa gaacgcctca   240
tcctccaact ccatgctcng tggggaaaca agtggtccaa ggataacacg gaactgccaa   300
ggcgtancga caatgaatna aagaactact gggagaacac atttgaggaa aaggaag     357

<210> SEQ ID NO 56
<211> LENGTH: 54
<212> TYPE: PRT
<213> ORGANISM: Triticum aestivum
<220> FEATURE:
<221> NAME/KEY: UNSURE
<222> LOCATION: (21)
<223> OTHER INFORMATION: Xaa can be any naturally occurring amino acid
<220> FEATURE:
<221> NAME/KEY: UNSURE
<222> LOCATION: (27)..(28)
<223> OTHER INFORMATION: Xaa can be any naturally occurring amino acid
<220> FEATURE:
<221> NAME/KEY: UNSURE
<222> LOCATION: (41)
<223> OTHER INFORMATION: Xaa can be any naturally occurring amino acid

<400> SEQUENCE: 56

Ala Gly Leu Asn Arg Thr Gly Lys Ser Cys Arg Leu Arg Trp Val Asn
 1               5                  10                  15

Tyr Leu His Pro Xaa Leu Lys Arg Gly Arg Xaa Xaa Pro Met Lys Glu
             20                  25                  30

Arg Leu Ile Leu Gln Leu His Ala Xaa Trp Gly Asn Lys Trp Ser Lys
         35                  40                  45

Asp Asn Thr Glu Leu Pro
     50

<210> SEQ ID NO 57
<211> LENGTH: 1072
<212> TYPE: DNA
<213> ORGANISM: Triticum aestivum

<400> SEQUENCE: 57
gcacgaggcc aaagtatcag gtttgagggg tggggatcc aaaaattagg tagctatatt    60

```
gaagtatttt gcgcaaagtc gcaacaacaa atgtcacctt tgctaataac tttcttcttg      120
cttcaacctc tgtaatctcc atgcaggcct caaccgcaca ggaaagagct gtcgcctccg      180
gtgggttaac tacctccacc ctggcctaaa gcgtgggcgc atgactcccc atgaagaacg      240
cctcatcctc gagctccatg ctcggtgggg aaacaggtgg tccaggatag cacggaagct      300
gccagggcgt accgacaatg agatcaagaa ctactggaga acacatatga ggaagaaagc      360
acaggagagg aagaggagcg tgtcaccctc accatcttca tcctcagtga cataccaatc      420
cattcagcca cagacgccat cgatcatggg aattggcgag caggaacttc atggtggcag      480
tagctgcatc acaagcatat tgaagggcac gcctgctgac atggatggat acctcatgga      540
tcagatatgg atggagattg aggcaccctc tggggtcaac tttcatgacg ggaaggataa      600
ttcatacagc agccctctg gccctctgct gccatcaccg atgtgggatt actacagccc       660
tgaggcaggc tggaagatgg atgagataaa gatggcccca caagttagct acagtaaagg      720
aattggcccc agttattgaa gccatatata ttgtatcaga ttactaagtt acttgcaacc      780
tagcagaagt gaaatgcttt tgttgaaaga accattagca tggatctaaa aaatatttat      840
atctatctag cattccaagt gtgctcatgt tttatgtatc tactatgtag catctagtgt      900
gcaagacatg taatgcaagg acacttccac tttgtattca caataatcag ctatctcctg      960
taagactttt ccaatgcaaa catgattagc aggtgtaata tcaacttaaa tgcttgccaa     1020
aaaaaaaaaa aaaaaaaaa aaaaaaaaa aaaaaaaaa aaaaaaaaa aa                 1072
```

<210> SEQ ID NO 58
<211> LENGTH: 198
<212> TYPE: PRT
<213> ORGANISM: Triticum aestivum

<400> SEQUENCE: 58

```
Ala Gly Leu Asn Arg Thr Gly Lys Ser Cys Arg Leu Arg Trp Val Asn
 1               5                  10                  15

Tyr Leu His Pro Gly Leu Lys Arg Gly Arg Met Thr Pro His Glu Glu
            20                  25                  30

Arg Leu Ile Leu Glu Leu His Ala Arg Trp Gly Asn Arg Trp Ser Arg
        35                  40                  45

Ile Ala Arg Lys Leu Pro Gly Arg Thr Asp Asn Glu Ile Lys Asn Tyr
    50                  55                  60

Trp Arg Thr His Met Arg Lys Lys Ala Gln Glu Arg Lys Arg Ser Val
65                  70                  75                  80

Ser Pro Ser Pro Ser Ser Ser Val Thr Tyr Gln Ser Ile Gln Pro
                85                  90                  95

Gln Thr Pro Ser Ile Met Gly Ile Gly Glu Gln Glu Leu His Gly Gly
           100                 105                 110

Ser Ser Cys Ile Thr Ser Ile Leu Lys Gly Thr Pro Ala Asp Met Asp
       115                 120                 125

Gly Tyr Leu Met Asp Gln Ile Trp Met Glu Ile Glu Ala Pro Ser Gly
   130                 135                 140

Val Asn Phe His Asp Gly Lys Asp Asn Ser Tyr Ser Ser Pro Ser Gly
145                 150                 155                 160

Pro Leu Leu Pro Ser Pro Met Trp Asp Tyr Tyr Ser Pro Glu Ala Gly
               165                 170                 175

Trp Lys Met Asp Glu Ile Lys Met Ala Pro Gln Val Ser Tyr Ser Lys
           180                 185                 190

Gly Ile Gly Pro Ser Tyr
```

<210> SEQ ID NO 59
<211> LENGTH: 521
<212> TYPE: DNA
<213> ORGANISM: Triticum aestivum
<220> FEATURE:
<221> NAME/KEY: unsure
<222> LOCATION: (108)
<223> OTHER INFORMATION: n is a, c, g or t
<220> FEATURE:
<221> NAME/KEY: unsure
<222> LOCATION: (355)
<223> OTHER INFORMATION: n is a, c, g or t
<220> FEATURE:
<221> NAME/KEY: unsure
<222> LOCATION: (361)
<223> OTHER INFORMATION: n is a, c, g or t
<220> FEATURE:
<221> NAME/KEY: unsure
<222> LOCATION: (392)
<223> OTHER INFORMATION: n is a, c, g or t
<220> FEATURE:
<221> NAME/KEY: unsure
<222> LOCATION: (414)
<223> OTHER INFORMATION: n is a, c, g or t
<220> FEATURE:
<221> NAME/KEY: unsure
<222> LOCATION: (431)
<223> OTHER INFORMATION: n is a, c, g or t
<220> FEATURE:
<221> NAME/KEY: unsure
<222> LOCATION: (434)
<223> OTHER INFORMATION: n is a, c, g or t
<220> FEATURE:
<221> NAME/KEY: unsure
<222> LOCATION: (447)
<223> OTHER INFORMATION: n is a, c, g or t
<220> FEATURE:
<221> NAME/KEY: unsure
<222> LOCATION: (456)
<223> OTHER INFORMATION: n is a, c, g or t
<220> FEATURE:
<221> NAME/KEY: unsure
<222> LOCATION: (459)
<223> OTHER INFORMATION: n is a, c, g or t

<400> SEQUENCE: 59

```
cttggatcct ccactagcta cgtcgtccat ggatgtggtg ctgcagagtc gtagcagcaa      60
cagcatggcg gcggagccgg aggaggaggc ggaccggagg aggaggcngg agctccggcg     120
agggccgtgg acggtggacg aggaccttac gctgatcaac tacatcgcgg accacgcga     180 gggccgctgg aacgcgctgg cgcgggccgc cggcctgagg cgcacgggga agagctgccg    240
gctgcggtgg ctgaactacc tccgccccga cgtgaagcgc ggcaacttca ccgccgacga    300
gcagctcctc atcctcgacc tccactctcg ctggggcaac cggtggtcga agatngcgca    360
ncacctcccg ggtcggacgg acaacgaaga tnaaagaact actgggagga ccanggtgca    420
aaaagcacgc naancaactc aactgcnaac tccggnaanc gcaaccttta aaggatgcca    480
ataaggtacc tctggatgcc tcgcctctca acgcatcaac c                        521
```

<210> SEQ ID NO 60
<211> LENGTH: 131
<212> TYPE: PRT
<213> ORGANISM: Triticum aestivum
<220> FEATURE:
<221> NAME/KEY: UNSURE
<222> LOCATION: (27)
<223> OTHER INFORMATION: Xaa can be any naturally occurring amino acid
<220> FEATURE:
<221> NAME/KEY: UNSURE
<222> LOCATION: (109)
<223> OTHER INFORMATION: Xaa can be any naturally occurring amino acid
<220> FEATURE:
<221> NAME/KEY: UNSURE
<222> LOCATION: (111)
<223> OTHER INFORMATION: Xaa can be any naturally occurring amino acid
<220> FEATURE:
<221> NAME/KEY: UNSURE
<222> LOCATION: (122)
<223> OTHER INFORMATION: Xaa can be any naturally occurring amino acid
<220> FEATURE:
<221> NAME/KEY: UNSURE
<222> LOCATION: (129)
<223> OTHER INFORMATION: Xaa can be any naturally occurring amino acid

<400> SEQUENCE: 60

Met Asp Val Val Leu Gln Ser Arg Ser Asn Ser Met Ala Ala Glu
1               5                   10                  15

Pro Glu Glu Glu Ala Asp Arg Arg Arg Xaa Glu Leu Arg Arg Gly
                20                  25                  30

Pro Trp Thr Val Asp Glu Asp Leu Thr Leu Ile Asn Tyr Ile Ala Asp
                35                  40                  45

His Gly Glu Gly Arg Trp Asn Ala Leu Ala Arg Ala Ala Gly Leu Arg
        50                  55                  60

Arg Thr Gly Lys Ser Cys Arg Leu Arg Trp Leu Asn Tyr Leu Arg Pro
65              70                  75                  80

Asp Val Lys Arg Gly Asn Phe Thr Ala Asp Glu Gln Leu Leu Ile Leu
                85                  90                  95

Asp Leu His Ser Arg Trp Gly Asn Arg Trp Ser Lys Xaa Ala Xaa His
                100                 105                 110

Leu Pro Gly Arg Thr Asp Asn Glu Asp Xaa Arg Thr Thr Gly Arg Thr
                115                 120                 125

Xaa Val Gln
    130

<210> SEQ ID NO 61
<211> LENGTH: 464
<212> TYPE: DNA
<213> ORGANISM: Triticum aestivum
<220> FEATURE:
<221> NAME/KEY: unsure
<222> LOCATION: (435)
<223> OTHER INFORMATION: n is a, c, g or t
<220> FEATURE:
<221> NAME/KEY: unsure
<222> LOCATION: (442)
<223> OTHER INFORMATION: n is a, c, g or t
<220> FEATURE:
<221> NAME/KEY: unsure
<222> LOCATION: (450)
<223> OTHER INFORMATION: n is a, c, g or t
<220> FEATURE:
<221> NAME/KEY: unsure
<222> LOCATION: (457)
<223> OTHER INFORMATION: n is a, c, g or t

<400> SEQUENCE: 61
agcgggcgag acgtgagcat ggggaggccg ccgtgctgcg acaaggaggg cgtcaagaag      60
ggcccctgga cgccggagga ggacctcgtg ctcgtctcct acgtccagga gcacggcccc     120
ggcaactggc gcgccgtccc caccaggacc ggcctgatgc ggtgtagcaa gagctgccgg     180
ctccggtgga ccaactacct gcgcccaggg atcaagcgcg caacttcac cgaccaggag      240 gagaagctca tcgtccacct ccaggcgctg ctcggcaaca ggtgggccgc gatcgcctcc     300
tacctccccg agcgcaccga caacgacatc aagaactact ggaacacgca actcaagcgc     360

```
aagctgcaag cggggggcga cgccgcgggc aaaccggcgg cgcaaaggct gctcctcctc    420
aaagggcaat ggganaggcg gngcagacgn catcaanatg cgcc                    464
```

<210> SEQ ID NO 62
<211> LENGTH: 122
<212> TYPE: PRT
<213> ORGANISM: Triticum aestivum

<400> SEQUENCE: 62

```
Met Gly Arg Pro Pro Cys Cys Asp Lys Glu Gly Val Lys Lys Gly Pro
 1               5                   10                  15

Trp Thr Pro Glu Glu Asp Leu Val Leu Val Ser Tyr Val Gln Glu His
                20                  25                  30

Gly Pro Gly Asn Trp Arg Ala Val Pro Thr Arg Thr Gly Leu Met Arg
            35                  40                  45

Cys Ser Lys Ser Cys Arg Leu Arg Trp Thr Asn Tyr Leu Arg Pro Gly
        50                  55                  60

Ile Lys Arg Gly Asn Phe Thr Asp Gln Glu Glu Lys Leu Ile Val His
65                  70                  75                  80

Leu Gln Ala Leu Leu Gly Asn Arg Trp Ala Ala Ile Ala Ser Tyr Leu
                85                  90                  95

Pro Glu Arg Thr Asp Asn Asp Ile Lys Asn Tyr Trp Asn Thr Gln Leu
            100                 105                 110

Lys Arg Lys Leu Gln Ala Gly Gly Asp Ala
        115                 120
```

<210> SEQ ID NO 63
<211> LENGTH: 217
<212> TYPE: PRT
<213> ORGANISM: Pisum sativum

<400> SEQUENCE: 63

```
Met Asp Lys Lys Pro Cys Asn Ser Ser Gln Asp Pro Glu Val Arg Lys
 1               5                   10                  15

Gly Pro Trp Thr Met Glu Glu Asp Leu Ile Leu Ile Asn Tyr Ile Ala
                20                  25                  30

Asn His Gly Glu Gly Val Trp Asn Ser Leu Ala Lys Ala Ala Gly Leu
            35                  40                  45

Lys Arg Thr Gly Lys Ser Cys Arg Leu Arg Trp Leu Asn Tyr Leu Arg
        50                  55                  60

Pro Asp Val Arg Arg Gly Asn Ile Thr Pro Glu Glu Gln Leu Leu Ile
65                  70                  75                  80

Met Glu Leu His Ser Lys Trp Gly Asn Arg Trp Ser Lys Ile Ala Lys
                85                  90                  95

His Leu Pro Gly Arg Thr Asp Asn Glu Ile Lys Asn Phe Trp Arg Thr
            100                 105                 110

Arg Ile Gln Lys His Ile Lys Gln Val Asp Asn Pro Asn Gln Gln Asn
        115                 120                 125

Phe Gln Gln Lys Met Ser Leu Glu Ile Asn Asp His His His His
        130                 135                 140

Pro His Gln Pro Ser Ser Gln Val Ser Asn Leu Val Glu Pro Met
145                 150                 155                 160

Glu Thr Tyr Ser Pro Thr Ser Tyr Gln Gly Thr Leu Glu Pro Phe Pro
                165                 170                 175

Thr Gln Phe Pro Thr Ile Asn Asn Asp His His Gln Asn Ser Asn Cys
```

-continued

```
                180                 185                 190
Cys Ala Asn Asp Asn Asn Asn Asn Tyr Trp Ser Met Glu Asp Ile
        195                 200                 205

Trp Ser Met Gln Leu Leu Asn Gly Asp
    210                 215
```